(12) United States Patent
Duffy

(10) Patent No.: US 6,451,555 B1
(45) Date of Patent: Sep. 17, 2002

(54) NUCLEIC ACIDS THAT ENCODE TESTES SPECIFIC PROTEASE AND DETECT DNA HYPOMETHYLATED IN CANCER CELLS

(75) Inventor: Hao-Peng Xu Duffy, Centerport, NY (US)

(73) Assignee: North Shore-Long Island Jewish Research Institute, Manhasset, NY (US)

( * ) Notice: Subject to any disclaimer, the term of this patent is extended or adjusted under 35 U.S.C. 154(b) by 0 days.

(21) Appl. No.: 09/163,951

(22) Filed: Sep. 30, 1998

Related U.S. Application Data

(63) Continuation-in-part of application No. 08/657,866, filed on May 31, 1996, now Pat. No. 5,871,917.

(51) Int. Cl.[7] .......................... C12P 21/06; C07H 21/04; C12N 1/21; C12N 15/63; C12N 5/10
(52) U.S. Cl. ................ 435/69.1; 435/252.3; 435/320.1; 435/325; 435/810; 536/23.5; 536/24.31; 536/24.33; 536/23.2
(58) Field of Search .............................. 536/23.2, 23.5, 536/24.31, 24.33; 435/69.1, 252.3, 320.1, 325, 810

(56) References Cited

U.S. PATENT DOCUMENTS

| | | | |
|---|---|---|---|
| 5,436,142 A | 7/1995 | Wigler et al. | 435/91.2 |
| 5,552,277 A | 9/1996 | Nelson et al. | 435/6 |
| 5,756,668 A | 5/1998 | Baylin et al. | 530/350 |
| 5,786,146 A | 7/1998 | Herman et al. | 435/6 |
| 5,811,238 A | 9/1998 | Stemmer et al. | 435/6 |
| 5,846,712 A | 12/1998 | Baylin | 435/6 |
| 5,856,094 A | 1/1999 | Sidransky et al. | 435/6 |

FOREIGN PATENT DOCUMENTS

| | | |
|---|---|---|
| EP | 0 814 158 | 12/1997 |
| EP | 0814158 A2 * | 12/1997 |
| WO | WO 97/45560 | 12/1997 |
| WO | WO 9746705 A1 | 12/1997 |
| WO | WO 9805782 A1 | 2/1998 |
| WO | WO 9854318 A1 | 12/1998 |
| WO | WO 9856952 A1 | 12/1998 |

OTHER PUBLICATIONS

Hillier, L. et al. EST Accession No. AA203189, Jan. 1997.*
Parkhill, J. GenEmbl Accession No. Z81368, Jun. 1998.*
Belinsky, S.A., Nikula, K.J., Baylin, S.B. and Issa, J.P. (1996) Increased cytosine DNA–methyltransferase activity is target–cell–specific and an early event in lung cancer. Proc. Natl. Acad. Sci. U.S.A. 93:4045–4050.
Braun, B.S., Frieden, R., Lessnick, S.L., May, W.A. and Denny, C.T. (1995) Identification of target genes for the Ewing's sarcoma EWS/FLI fusion protein by representational difference analysis. Mol. Cell. Biol. 15:4623–4630.
Chang, Y., Cesarman, E., Pessin, M.S., Lee, F., Culpepper, J., Knowles, D.M. and Moore, P.S. (1994) Identification of herpesvirus–like DNA sequences in AIDS–associated Kaposi's sarcoma. Science 266:1865–1869.
Hillier et al., "The WashU–Merck Project", unpublished, Jan. 24, 1997, Database EST, EST Accession No. AA203189.
Janeway, Jr. et al., "Immunobiology: the immune system in health and disease", Current Biology Ltd./Garland Publishing Inc., 1994, pp. 2:24, 2:41.
Clark, S.J., Harrison, J. and Frommer, M. (1995) CpNpG methylation in mammalian cells. Nat. Genet. 10:20–27.
Costello, J.F., Berger, M.S., Huangm H.S. and Cavenee, W.K. (1996) Silencing of p16/CDKN2 expression in human gliomas by methylation and chromatin condensation. Cancer Res. 56:2405–2410.
Frommer, M., McDonald, L.E., Millar, D.S., Collis, C.M., Watt, F., Grigg, G.W., Molloy, P.L. and Paul, C.L. (1992) A genomic sequencing protocol that yields a positive display of 5–methylcytosine residues in individual DNA strands. Proc. Natl. Acad. Sci. U.S.A. 89:1827–1831.
Gonzalgo, M.L., Liang, G., Spruck, C.H. 3rd, Zingg, J.M., Rideout, W.M. 3rd and Jones, P.A. (1997) Identification and characterization of differentially methylated regions of genomic DNA by methylation–sensitive arbitrarily primed PCR. Cancer Res. 57:594–599.
Graff, J.R., Herman, J.G., Lapidus, R.G., Chopra, H., Xu, R., Jarrard, D.F., Isaacs, W.B., Pitha, P.M., Davidson, N.E. and Baylin, S.B. (1995) E–cadherin expression in silenced by DNA hypermethylation in human breast and prostate carcinomas. Cancer Res. 55:5195–5199.

(List continued on next page.)

Primary Examiner—Diana Johannsen
(74) Attorney, Agent, or Firm—Kenyon & Kenyon

(57) ABSTRACT

The present invention provides Methyl- (or Mutant-) Differential Display (MDD) methods and nucleic acid probes for detecting mutations and the methylation patterns of nucleic acids. The methods of the present invention are particularly useful for detecting and isolating genomic DNA fragments which are near coding and regulatory regions of genes and which are differentially mutated or methylated relative to the corresponding DNA from normal cells. Genes are frequently not methylated in the cells where they are expressed but are methylated in cell types where they are not expressed. Moreover, tumor cell DNA is frequently methylated to a different extent and in different regions than is the DNA of normal cells. The present invention is used for identifying which regions of the genome are methylated or mutated in different cell types, including cancerous cell types. The present invention is also used for diagnosing whether a tissue sample is cancerous, and whether that cancerous condition is non-metastatic or metastatic.

18 Claims, 12 Drawing Sheets

OTHER PUBLICATIONS

Figure 1A:
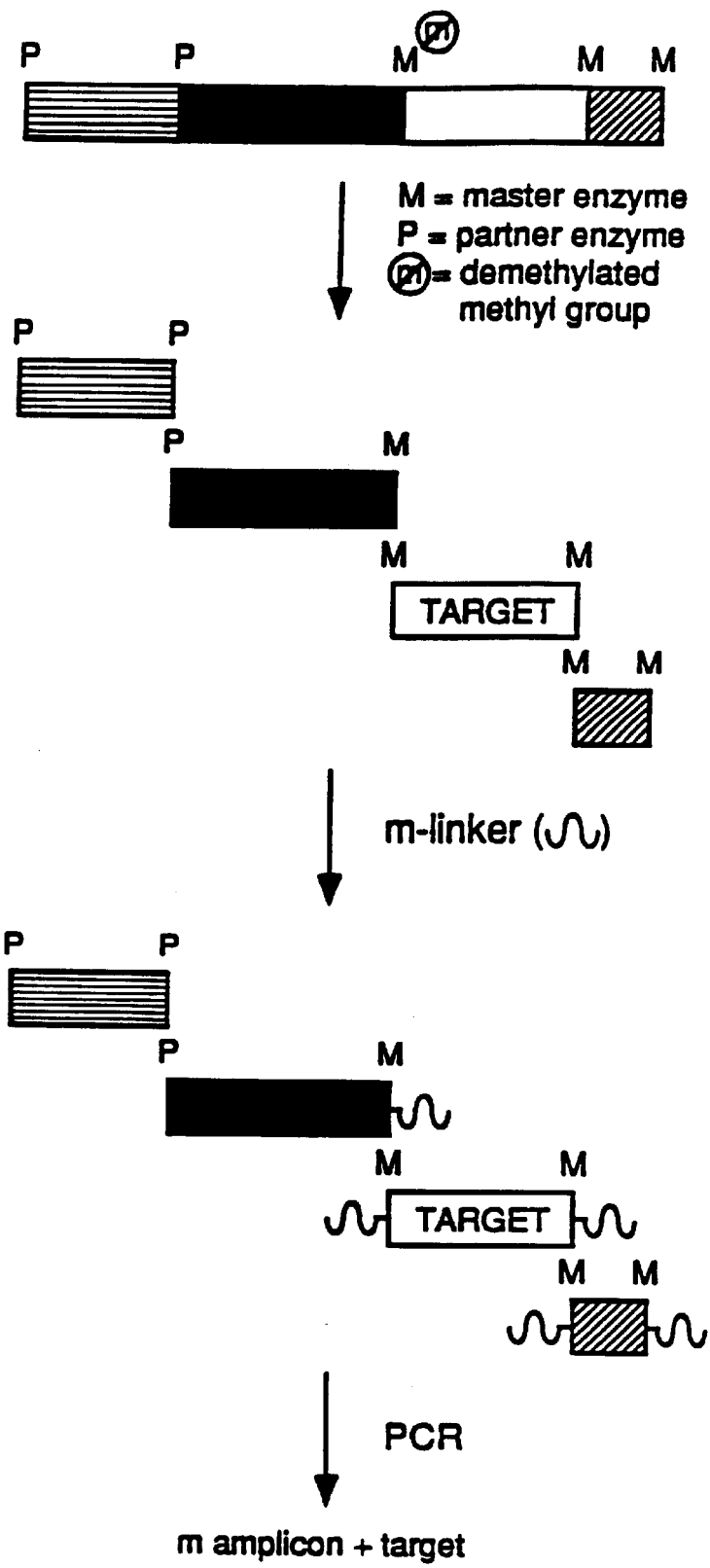

Hakkarainen, M., Wahlfors, J., Myohanen, S., Hiltunen, M.O., Eskelinen, M., Johansson, R. and Janne, J. (1996) Hypermethylation of calcitonin gene regulatory sequences in human breast cancer as revealed by genomic sequencing. Int. J. Cancer 69(6):471–4.

Herman, J.G., Graff, J.R., Myohanen, S., Nelkin, B.D. and Baylin, S.B. (1996) Methylation–specific PCR: a novel PCR assay for methylation status of CpG islands. Proc. Natl. Acad. Sci. U.S.A. 93:9821–9826.

Herman, J.G., Jen, J., Merlo, A. Baylin, S.B. (1996) Hypermethylation–associated inactivation indicates a tumor suppressor role for p15INK4B. Cancer Res. 56:722–727.

Horsthemke, B., Claussen, U., Hesse, S. and Ludecke, H.J. (1992) PCR–mediated cloning of HpaII tiny fragments from microdissected human chromosomes. PCR Methods Appl. 1:229–233.

Huang, T.H., Laux, D.E., Hamlin, B.C., Tran, P., Tran, H., Lubahn, D.B. (1997) Identification of DNA methylation markers for human breast carcinomas using the methylation–sensitive restriction fingerprinting technique. Cancer Res. 57:1030–1034.

Hubank, M. and Schatz, D.G. (1994) Identifying differences in mRNA expression by representational difference analysis of cDNA. Nucleic Acids Res. 22:5640–5648.

Huynh, H., Alpert, L. and Pollak, M. (1996) Silencing of the mammary–derived growth inhibitor (MDGI) gene in breast neoplasms is associated with epigenetic changes. Cancer Res. 56:4865–4870.

Issa, J.P., Zehnbauer, B.A., Civin, C.I., Collector, M.I., Sharkis, S.J., Davidson, N.E., Kaufmann, S.H. and Baylin, S.B. (1996) The estrogen receptor CpG island is methylated in most hematopoietic neoplasms. Cancer Res. 56:973–977.

Laird, P.W. and Jaenisch, R. (1994) DNA methylation and cancer. Hum. Mol. Genet. 3 Spec. No.:1487–1495.

Liang, G., Salem, C.E., Yu, M.C., Nguyen, H.D., Gonzales, F.A., Nguyen, T.T., Nichols, P.W. and Jones, P.A. (1998) DNA methylation differences associated with tumor tissues identified by genome scanning analysis. Genomics 53:260–268.

Lisitsyn, N., Lisitsyn, N. and Wigler, M. (1993) Cloning the differences between two complex genomes. Science 259:946–951.

Lisitsyn, N.A., Segre, J.A., Kusumi, K., Lisitsyn, N.M., Nadeau, J.H., Frankel, W.N., Wigler, M.H. and Lander, E.S. (1994) Direct isolation of polymorphic markers linked to a trait by genetically directed representational difference analysis. Nat. Genet. 6:57–63.

Little, M. and Wainwright, B. (1995) Methylation and p16: suppressing the suppressor. Nat. Med. 1:633–634.

Loebel, D.A.F. and Johnston, P.G. (1996) Methylation analysis of a marsupial X–linked CpG island by bisulfite genomic sequencing. Genome Res. 6:114–123.

McGrew, M.J. and Rosenthal, N. (1993) Quantitation of genomic methylation using ligation–mediated PCR. Biotechniques 15:722–729.

Merlo, A., Herman, J.G., Mao, L., Lee, D.J., Gabrielson, E., Burger, P.C., Baylin, S.B. and Sidransky, D. (1995) 5' CpG island methylation is associated with transcriptional silencing of the tumour suppressor p16/CDKN2/MTS1 in human cancers. Nat. Med. 1:686–692.

Parrish, J.E. and Nelson, D.L. (1993) Methods for finding genes. A major rate–limiting step in positional cloning. Genet. Anal. Tech. Appl. 10:29–41.

Singer–Sam, J., LeBon, J.M., Tanguay, R.L. and Riggs, A.D. (1990) A quantitative HpaII–PCR assay to measure methylation of DNA from a small number of cells. Nucleic Acids Res. 18:687.

Stiegerwald, C.D., Pfeifer, G.P. and Riggs, A.D. (1990) Ligation–mediated PCR improves the sensitivity of methylation analysis by restriction enzymes and detection of specific DNA strand breaks. Nucleic Acids Res. 18:1435–1439.

Wieland, I., Bolger, G., Asouline, G. and Wigler, M. (1990) A method for difference cloning: gene amplification following subtractive hybridization. Proc. Natl. Acad. Sci. U.S.A. 87:2720–2724.

Willison, K. (1991) Opposite imprinting of the mouse Igf2 and Igf2r genes. Trends Genet. 7:107–109.

Xu, H.P., Yanak, B.L., Wigler, M.H. and Gorin, M.B. (1996) New polymorphic markers in the vicinity of the pearl locus on mouse chromosome 13. Mamm. Genome 7:16–19.

* cited by examiner

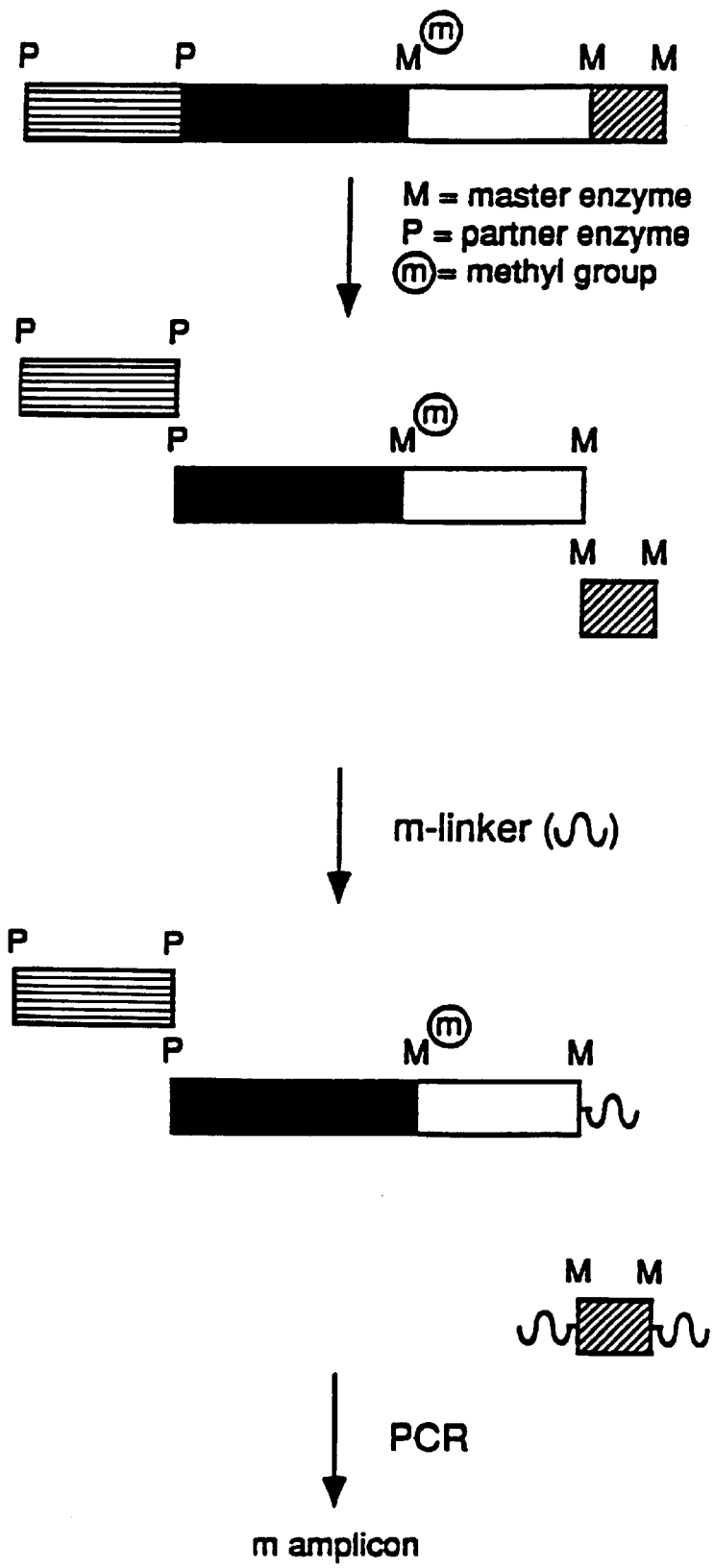
FIG. IB

SEQUENCE LISTING

```
<160> NUMBER OF SEQ ID NOS: 16

<210> SEQ ID NO 1
<211> LENGTH: 24
<212> TYPE: DNA
<213> ORGANISM: Artificial Sequence
<220> FEATURE:
<223> OTHER INFORMATION: Synthetic adapter

<400> SEQUENCE: 1
ctcgtcgtca ggtcagtgct tcac                                              24

<210> SEQ ID NO 2
<211> LENGTH: 12
<212> TYPE: DNA
<213> ORGANISM: Artificial Sequence
<220> FEATURE:
<223> OTHER INFORMATION: Synthetic adapter

<400> SEQUENCE: 2
cggtgaagca ct                                                           12

<210> SEQ ID NO 3
<211> LENGTH: 24
<212> TYPE: DNA
<213> ORGANISM: Artificial Sequence
<220> FEATURE:
<223> OTHER INFORMATION: Synthetic adapter

<400> SEQUENCE: 3
tagagccacg tagctgctgt agtc                                              24

<210> SEQ ID NO 4
<211> LENGTH: 12
<212> TYPE: DNA
<213> ORGANISM: Artificial Sequence
<220> FEATURE:
<223> OTHER INFORMATION: Synthetic adapter

<400> SEQUENCE: 4
cggactacag ca                                                           12

<210> SEQ ID NO 5
<211> LENGTH: 24
<212> TYPE: DNA
<213> ORGANISM: Artificial Sequence
<220> FEATURE:
<223> OTHER INFORMATION: Synthetic adapter

<400> SEQUENCE: 5
accgtggact ggataggttc agac                                              24

<210> SEQ ID NO 6
<211> LENGTH: 12
<212> TYPE: DNA
<213> ORGANISM: Artificial Sequence
<220> FEATURE:
<223> OTHER INFORMATION: Synthetic adapter
```

<400> SEQUENCE: 6
cggtctgaac ct                                                              12

<210> SEQ ID NO 7
<211> LENGTH: 309
<212> TYPE: DNA
<213> ORGANISM: Homo sapiens

<400> SEQUENCE: 7
ccggggcccc acaggccccg tgctgaaaca gggctggaac caggcaactt gtttctttgt           60
cctgacatcc ctgcgcagct ggtaccgagt ggacagcccc aacaaactca tgaacccgct          120
ggtcgctggg gtcttcggag ccattgtggg agcggccagt gtcttcggaa atgctcctct          180
gcacgagatc gagccccaga tgcgggacct ggaggtgcac aaatgcataa cacatgggac          240
tgtggctgca aatcctgagg gaagggcaca agaccttcct acaagggcac tattgcccgc          300
ctgggccgg                                                                 309

<210> SEQ ID NO 8
<211> LENGTH: 332
<212> TYPE: DNA
<213> ORGANISM: Homo sapiens

<400> SEQUENCE: 8
ccgggcaatc tccacaggca ctccttccac tgtctgtaca acgtccttag ctcttccttc           60
tgcccagtgt gcaatcttcc cagatgggcc ttctgccaca cattcacgtc tgatctggca          120
ggtgtttctt ctgccaaacc ttcatccttc tcggatgctc ttctgccaca tgtgcaatcc          180
tgtcagacgt tcctgccact cgaggtagct ggtctgatgt gagcatggaa ccaggggtc           240 cccctaccac caccaggaat gtcagatgat catgaggtgt cggttgggcg gttcttgaac          300
cctatctatg gaggataacc gctcacggcc gg                                       332

<210> SEQ ID NO 9
<211> LENGTH: 568
<212> TYPE: DNA
<213> ORGANISM: Homo sapiens

<400> SEQUENCE: 9
ccggcctggg aggagggttc ccaccaggct ttctcaagcc catcacaagt gagtcaggaa           60
ccatctccca ttggtcctgg taaggaggag atttggagga aggactggga agcctgtgga          120 gcggagggt actgggggtg gaagtggaag aaggtggcac agtaacagac tcccttctcc          180
tgagattccc agcatggatt ggaggggctg ccctgcagcg tcccttaccc cttgttacct          240
ggcagcctgc aagtagctct agggccagcc atgtggtcac ctacatctgt tgggggagag          300
aaggaaaaca gatgccccga gtcgtagaga cttgcattat cagcccctgg gtccaacagc          360
aagtgagcta agcacttgca aatgttatct gatgtattct ttataagaag gggtcacaaa          420
actgagactt agaacatgta agaggagac agggatttga gcctggatca gctatgtgag           480
gatctcctgt ctgtccccgc tggttccaat tcaggtctta gagtaaaagg gttggggatg          540
agctctctgg caggacagtg ccctccgg                                            568

<210> SEQ ID NO 10
<211> LENGTH: 1005
<212> TYPE: DNA
<213> ORGANISM: Homo sapiens -continued

```
<400> SEQUENCE: 10
ccggaggcag gcacaggact cgggagggac gctgccagct ctctgggtgc tgagttcaca    60
aggctgcatt catgattttc aatagacctg tgatggtctg tgcccagtgc tggggacaca   120
gaagagtcaa acctggctcc tgacctggac ctggatcatc acgtgacagg gaggagagcg   180
atccaggctg atgaggaaag cgcatgacat ggggtcttag gagcagtgag gggcagagcc   240
atggccaaag gccccgccat ggaagctgag gactctggca ccagatggag gcagttgacc   300
gacctctgcc cttggggtcc aacccatggg cttctcatac ataggggtga aaaaggccat   360
tctatttatg cagaattttc ccatgtggcc aggcagcaga agtccagagg ggtaggggcc   420
actcagggtc acacagaaca gcagttgctg aagactgggg aagtccaggc ctaggctcca   480
cctgcccttc ccctgacatg ggccaccac tagccttta tgggcaggcc tggctgctgg    540
tggttggaat aacatctgac tccagtgggt gtctgtcacc gtctccagac aggagacaga   600
gacagagggt caaagttcac tatggctctt tggggcaatg aaatgctgtg ttctagcctc   660
ttgccagaaa tcagccaaag tcaaggaaag cctgactccc acagttatca cagaaagagc   720
acccactttc cagcccagac agctgcaccc cagctgggtc ctggcagccc cagcttcagc   780
ctgggcggta tgttccaggc ccctcgatca tctgacccta atatcacccc ttcacacccc   840
ctccactttc tgcgggagcc accccgaacc tttgaatggg ggagatcctg gaggctctgc   900
aattttcagt gtaaactgcc tggagttccc cacttcaccc tcatctggtt cacctgtgga   960
ctcccaacag agcaggccca ggaaacgcgg ggcctctgag gccgg               1005

<210> SEQ ID NO 11
<211> LENGTH: 17
<212> TYPE: DNA
<213> ORGANISM: Artificial Sequence
<220> FEATURE:
<223> OTHER INFORMATION: Synthetic primer

<400> SEQUENCE: 11
cctggatggt cagcgtg                                                   17

<210> SEQ ID NO 12
<211> LENGTH: 18
<212> TYPE: DNA
<213> ORGANISM: Artificial Sequence
<220> FEATURE:
<223> OTHER INFORMATION: Synthetic primer

<400> SEQUENCE: 12
cagtgttggt aggaggag                                                  18

<210> SEQ ID NO 13
<211> LENGTH: 682
<212> TYPE: DNA
<213> ORGANISM: Homo Sapiens
<220> FEATURE:
<223> OTHER INFORMATION: Synthetic probe

<400> SEQUENCE: 13
cctggatggt cagcgtgcgg gccaatggca cacacatctg tgccggcacc atcattgcct    60
cccagtgggt gctgactgtg gcccactgcc tgatctggcg tgatgttatc tactcagtga   120
gggtggggag tccgtggatt gaccagatga cgcagaccgc ctccgatgtc ccggtgctcc   180
aggtcatcat gcatagcagg taccgggccc agcggttctg tcctgggtg gccaggcca    240
acgacatcgg cctcctcaag ctcaagcagg aactcaagta cagcaattac gtgcggccca   300
```

```
tctgcctgcc tggcacggac tatgtgttga aggaccattc ccgctgcact gtgacgggct    360
ggggactttc caaggctgac ggcatgtggc ctcagttccg gaccattcag gagaaggaag    420
tcatcatcct gaacaacaaa gagtgtgaca atttctacca caacttcacc aaaatcccca    480
ctctggttca gatcatcaag tcccagatga tgtgtgcgga ggacacccac agggagaagt    540
tctgctatga gctaactgga gagcccttgg tctgctccat ggagggcacg tggtacctgg    600
tgggattggt gagctggggt gcaggctgcc agaagagcga ggccccaccc atctacctac    660
aggtctcctc ctaccaacac tg                                            682

<210> SEQ ID NO 14
<211> LENGTH: 1240
<212> TYPE: DNA
<213> ORGANISM: Homo sapiens
<220> FEATURE:
<221> NAME/KEY: CDS
<222> LOCATION: 60..1214
<220> FEATURE:
<223> OTHER INFORMATION: cDNA

<400> SEQUENCE: 14 gtcgtgggggg cggcactggg agcgccttcc ggagagacgc agtcggctgc caccccggg      59 atg ggt cgc tgg tgc cag acc gtc gcg cgc ggg cag cgc ccc cgg acg     107
Met Gly Arg Trp Cys Gln Thr Val Ala Arg Gly Gln Arg Pro Arg Thr
                 5                  10                  15 tct gcc ccc tcc cgc gcc ggt gcc ctg ctg ctg ctg ctt ctg ttg ctg     155
Ser Ala Pro Ser Arg Ala Gly Ala Leu Leu Leu Leu Leu Leu Leu Leu
             20                  25                  30 agg tct gca ggt tgc tgg ggc gca ggg gaa gcc ccg ggg gcg ctg tcc     203
Arg Ser Ala Gly Cys Trp Gly Ala Gly Glu Ala Pro Gly Ala Leu Ser
         35                  40                  45 act gct gat ccc gcc gac cag agc gtc cag tgt gtc ccc aag gcc acc     251
Thr Ala Asp Pro Ala Asp Gln Ser Val Gln Cys Val Pro Lys Ala Thr
     50                  55                  60 tgt cct tcc agc cgg cct cgc ctt ctc tgg cag acc ccg acc acc cag     299
Cys Pro Ser Ser Arg Pro Arg Leu Leu Trp Gln Thr Pro Thr Thr Gln
 65                  70                  75                  80 aca ctg ccc tcg acc acc atg gag acc caa ttc cca gtt tct gaa ggc     347
Thr Leu Pro Ser Thr Thr Met Glu Thr Gln Phe Pro Val Ser Glu Gly
                 85                  90                  95 aaa gtc gac cca tac cgc tcc tgt ggc ttt tcc tac gag cag gac ccc     395
Lys Val Asp Pro tyr Arg Ser Cys Gly Phe Ser tyr Glu Gln Asp Pro
            100                 105                 110 acc ctc agg gac cca gaa gcc gtg gct cgg cgg tgg ccc tgg atg gtc     443
Thr Leu Arg Asp Pro Glu Ala Val Ala Arg Arg Trp Pro Trp Met Val
        115                 120                 125 agc gtg cgg gcc aat ggc aca cac atc tgt gcc ggc acc atc att gcc     491
Ser Val Arg Ala Asn Gly Thr His Ile Cys Ala Gly Thr Ile Ile Ala
    130                 135                 140 tcc cag tgg gtg ctg act gtg gcc cac tgc ctg atc tgg cgt gat gtt     539
Ser Gln Trp Val Leu Thr Val Ala His Cys Leu Ile Trp Arg Asp Val
145                 150                 155                 160 atc tac tca gtg agg gtg ggg agt ccg tgg att gac cag atg acg cag     587
Ile tyr Ser Val Arg Val Gly Ser Pro Trp Ile Asp Gln Met Thr Gln
                165                 170                 175 acc gcc tcc gat gtc ccg gtg ctc cag gtc atc atg cat agc agg tac     635
Thr Ala Ser Asp Val Pro Val Leu Gln Val Ile Met His Ser Arg Tyr
            180                 185                 190
```

```
cgg gcc cag cgg ttc tgg tcc tgg gtg ggc cag gcc aac gac atc ggc    683
Arg Ala Gln Arg Phe Trp Ser Trp Val Gly Gln Ala Asn Asp Ile Gly
        195                 200                 205 ctc ctc aag ctc aag cag gaa ctc aag tac agc aat tac gtg cgg ccc    731
Leu Leu Lys Leu Lys Gln Glu Leu Lys tyr Ser Asn tyr Val Arg Pro
    210                 215                 220 atc tgc ctg cct ggc acg gac tat gtg ttg aag gac cat tcc cgc tgc    779
Ile Cys Leu Pro Gly Thr Asp tyr Val Leu Lys Asp His Ser Arg Cys
225                 230                 235                 240 act gtg acg ggc tgg gga ctt tcc aag gct gac ggc atg tgg cct cag    827
Thr Val Thr Gly Trp Gly Leu Ser Lys Ala Asp Gly Met Trp Pro Gln
            245                 250                 255 ttc cgg acc att cag gag aag gaa gtc atc atc ctg aac aac aaa gag    875
Phe Arg Thr Ile Gln Glu Lys Glu Val Ile Ile Leu Asn Asn Lys Glu
        260                 265                 270 tgt gac aat ttc tac cac aac ttc acc aaa atc ccc act ctg gtt cag    923
Cys Asp Asn Phe tyr His Asn Phe Thr Lys Ile Pro Thr Leu Val Gln
    275                 280                 285 atc atc aag tcc cag atg atg tgt gcg gag gac acc cac agg gag aag    971
Ile Ile Lys Ser Gln Met Met Cys Ala Glu Asp Thr His Arg Glu Lys
290                 295                 300 ttc tgc tat gag cta act gga gag ccc ttg gtc tgc tcc atg gag ggc   1019
Phe Cys tyr Glu Leu Thr Gly Glu Pro Leu Val Cys Ser Met Glu Gly
305                 310                 315                 320 acg tgg tac ctg gtg gga ttg gtg agc tgg ggt gca ggc tgc cag aag   1067
Thr Trp tyr Leu Val Gly Leu Val Ser Trp Gly Ala Gly Cys Gln Lys
            325                 330                 335 agc gag gcc cca ccc atc tac cta cag gtc tcc tcc tac caa cac tgg   1115
Ser Glu Ala Pro Pro Ile tyr Leu Gln Val Ser Ser tyr Gln His Trp
        340                 345                 350 atc tgg gac tgc ctc aac ggg cag gcc ctg gcc ctg cca gcc cca tcc   1163
Ile Trp Asp Cys Leu Asn Gly Gln Ala Leu Ala Leu Pro Ala Pro Ser
    355                 360                 365 agg acc ctg ctc ctg gca ctc cca ctg ccc ctc agc ctc ctt gct gcc   1211
Arg Thr Leu Leu Leu Ala Leu Pro Leu Pro Leu Ser Leu Leu Ala Ala
370                 375                 380 ctc tgactctgtg tgccctccc tcacttg                                  1240
Leu
385

<210> SEQ ID NO 15
<211> LENGTH: 1155
<212> TYPE: DNA
<213> ORGANISM: Homo sapiens
<220> FEATURE:
<221> NAME/KEY: CDS
<222> LOCATION: 1..1155
<220> FEATURE:
<223> OTHER INFORMATION: coding region of cDNA

<400> SEQUENCE: 15 tgg gtc gct ggt gcc aga ccg tcg cgc gcg ggc agc gcc ccg gga cgt     48
Met Gly Arg Trp Cys Gln Thr Val Ala Arg Gly Gln Arg Pro Arg Thr
        5                  10                  15 ctg ccc cct ccc gcg ccg gtg ccc tgc tgc tgc tgc ttc tgt tgc tga     96
Ser Ala Pro Ser Arg Ala Gly Ala Leu Leu Leu Leu Leu Leu Leu Leu
    20                  25                  30 ggt ctg cag gtt gct ggg gcg cag ggg aag ccc cgg ggg cgc tgt cca    144
Arg Ser Ala Gly Cys Trp Gly Ala Gly Glu Ala Pro Gly Ala Leu Ser
        35                  40                  45
```

```
ctg ctg atc ccg ccg acc aga gcg tcc agt gtg tcc cca agg cca cct       192
Thr Ala Asp Pro Ala Asp Gln Ser Val Gln Cys Val Pro Lys Ala Thr
     50                  55                  60 gtc ctt cca gcc ggc ctc gcc ttc tct ggc aga ccc gga cca ccc aga       240
Cys Pro Ser Ser Arg Pro Arg Leu Leu Trp Gln Thr Pro Thr Thr Gln
 65                  70                  75                  80 cac tgc cct cga cca cca tgg aga ccc aat tcc cag ttt ctg aag gca       288
Thr Leu Pro Ser Thr Thr Met Glu Thr Gln Phe Pro Val Ser Glu Gly
                     85                  90                  95 aag tcg acc cat acc gct cct gtg gct ttt cct acg agc agg acc cca       336
Lys Val Asp Pro tyr Arg Ser Cys Gly Phe Ser tyr Glu Gln Asp Pro
                100                 105                 110 ccc tca ggg acc cag aag ccg tgg ctc ggc ggt ggc cct gga tgg tca       384
Thr Leu Arg Asp Pro Glu Ala Val Ala Arg Arg Trp Pro Trp Met Val
            115                 120                 125 gcg tgc ggg cca atg gca cac aca tct gtg ccg gca cca tca ttg cct       432
Ser Val Arg Ala Asn Gly Thr His Ile Cys Ala Gly Thr Ile Ile Ala
        130                 135                 140 ccc agt ggg tgc tga ctg tgg ccc act gcc tga tct ggc gtg atg tta       480
Ser Gln Trp Val Leu Thr Val Ala His Cys Leu Ile Trp Arg Asp Val
145                 150                 155                 160 tct act cag tga ggg tgg gga gtc cgt gga ttg acc aga tga cgc aga       528
Ile tyr Ser Val Arg Val Gly Ser Pro Trp Ile Asp Gln Met Thr Gln
                165                 170                 175 ccg cct ccg atg tcc cgg tgc tcc agg tca tca tgc ata gca ggt acc       576
Thr Ala Ser Asp Val Pro Val Leu Gln Val Ile Met His Ser Arg Tyr
            180                 185                 190 ggg ccc agc ggt tct ggt cct ggg tgg gcc agg cca acg aca tcg gcc       624
Arg Ala Gln Arg Phe Trp Ser Trp Val Gly Gln Ala Asn Asp Ile Gly
        195                 200                 205 tcc tca agc tca agc agg aac tca agt aca gca att acg tgc ggc cca       672
Leu Leu Lys Leu Lys Gln Glu Leu Lys tyr Ser Asn tyr Val Arg Pro
210                 215                 220 tct gcc tgc ctg gca cgg act atg tgt tga agg acc att ccc gct gca       720
Ile Cys Leu Pro Gly Thr Asp tyr Val Leu Lys Asp His Ser Arg Cys
225                 230                 235                 240 ctg tga cgg gct ggg gac ttt cca agg ctg acg gca tgt ggc ctc agt       768
Thr Val Thr Gly Trp Gly Leu Ser Lys Ala Asp Gly Met Trp Pro Gln
                245                 250                 255 tcc gga cca ttc agg aga agg aag tca tca tcc tga aca aca agt           816
Phe Arg Thr Ile Gln Glu Lys Glu Val Ile Ile Leu Asn Asn Lys Glu
            260                 265                 270 gtg aca att tct acc aca act tca cca aaa tcc cca ctc tgg ttc aga       864
Cys Asp Asn Phe tyr His Asn Phe Thr Lys Ile Pro Thr Leu Val Gln
        275                 280                 285 tca tca agt ccc aga tga tgt gtg cgg agg aca ccc aca ggg aga agt       912
Ile Ile Lys Ser Gln Met Met Cys Ala Glu Asp Thr His Arg Glu Lys
290                 295                 300 tct gct atg agc taa ctg gag agc cct tgg tct gct cca tgg agg gca       960
Phe Cys tyr Glu Leu Thr Gly Glu Pro Leu Val Cys Ser Met Glu Gly
305                 310                 315                 320 cgt ggt acc tgg tgg gat tgg tga gct ggg gtg cag gct gcc aga aga      1008
Thr Trp tyr Leu Val Gly Leu Val Ser Trp Gly Ala Gly Cys Gln Lys
                325                 330                 335 gcg agg ccc cac cca tct acc tac agg tct cct cct acc aac act gga      1056
Ser Glu Ala Pro Pro Ile tyr Leu Gln Val Ser Ser tyr Gln His Trp
            340                 345                 350 tct ggg act gcc tca acg gca ggc cct ggc cct gca gcc cat cca          1104
Ile Trp Asp Cys Leu Asn Gly Gln Ala Leu Ala Leu Pro Ala Pro Ser
355                 360                 365
```

```
gga ccc tgc tcc tgg cac tcc cac tgc ccc tca gcc tcc ttg ctg ccc      1152
Arg Thr Leu Leu Leu Ala Leu Pro Leu Pro Leu Ser Leu Leu Ala Ala
    370                 375                 380 tct                                                                   1155
Leu
385

<210> SEQ ID NO 16
<211> LENGTH: 385
<212> TYPE: PRT
<213> ORGANISM: Homo sapiens

<400> SEQUENCE: 16

Met Gly Arg Trp Cys Gln Thr Val Ala Arg Gly Gln Pro Arg Thr
                5                  10                  15

Ser Ala Pro Ser Arg Ala Gly Ala Leu Leu Leu Leu Leu Leu Leu
             20                  25                  30

Arg Ser Ala Gly Cys Trp Gly Ala Gly Glu Ala Pro Gly Ala Leu Ser
             35                  40                  45

Thr Ala Asp Pro Ala Asp Gln Ser Val Gln Cys Val Pro Lys Ala Thr
     50                  55                  60

Cys Pro Ser Ser Arg Pro Arg Leu Leu Trp Gln Thr Pro Thr Thr Gln
65                  70                  75                  80

Thr Leu Pro Ser Thr Thr Met Glu Thr Gln Phe Pro Val Ser Glu Gly
                 85                  90                  95

Lys Val Asp Pro Tyr Arg Ser Cys Gly Phe Ser Tyr Glu Gln Asp Pro
            100                 105                 110

Thr Leu Arg Asp Pro Glu Ala Val Ala Arg Arg Trp Pro Trp Met Val
            115                 120                 125

Ser Val Arg Ala Asn Gly Thr His Ile Cys Ala Gly Thr Ile Ile Ala
130                 135                 140

Ser Gln Trp Val Leu Thr Val Ala His Cys Leu Ile Trp Arg Asp Val
145                 150                 155                 160

Ile Tyr Ser Val Arg Val Gly Ser Pro Trp Ile Asp Gln Met Thr Gln
                165                 170                 175

Thr Ala Ser Asp Val Pro Val Leu Gln Val Ile Met His Ser Arg Tyr
            180                 185                 190

Arg Ala Gln Arg Phe Trp Ser Trp Val Gly Gln Ala Asn Asp Ile Gly
            195                 200                 205

Leu Leu Lys Leu Lys Gln Glu Leu Lys Tyr Ser Asn Tyr Val Arg Pro
    210                 215                 220

Ile Cys Leu Pro Gly Thr Asp Tyr Val Leu Lys Asp His Ser Arg Cys
225                 230                 235                 240

Thr Val Thr Gly Trp Gly Leu Ser Lys Ala Asp Gly Met Trp Pro Gln
                245                 250                 255

Phe Arg Thr Ile Gln Glu Lys Glu Val Ile Ile Leu Asn Asn Lys Glu
            260                 265                 270

Cys Asp Asn Phe Tyr His Asn Phe Thr Lys Ile Pro Thr Leu Val Gln
            275                 280                 285

Ile Ile Lys Ser Gln Met Met Cys Ala Glu Asp Thr His Arg Glu Lys
    290                 295                 300

Phe Cys Tyr Glu Leu Thr Gly Glu Pro Leu Val Cys Ser Met Glu Gly
305                 310                 315                 320

Thr Trp Tyr Leu Val Gly Leu Val Ser Trp Gly Ala Gly Cys Gln Lys
                325                 330                 335
```

-continued

```
Ser Glu Ala Pro Pro Ile Tyr Leu Gln Val Ser Ser Tyr Gln His Trp
        340                 345             350

Ile Trp Asp Cys Leu Asn Gly Gln Ala Leu Ala Leu Pro Ala Pro Ser
            355             360             365

Arg Thr Leu Leu Leu Ala Leu Pro Leu Pro Leu Ser Leu Leu Ala Ala
    370                 375             380

Leu
385
```

NUCLEIC ACIDS THAT ENCODE TESTES SPECIFIC PROTEASE AND DETECT DNA HYPOMETHYLATED IN CANCER CELLS

RELATED U.S. APPLICATION DATA

This application is a continuation-in-part of U.S. Ser. No. 08/657,866, filed May 31, 1996, now U.S. Pat. No. 5,871,917, which is hereby incorporated by reference.

FIELD OF THE INVENTION

The present invention provides Methyl- (or Mutant-) Differential Display (MDD) methods and nucleic acid probes for detecting mutations and/or the methylation patterns of nucleic acids. Genes are frequently not methylated in the cells where they are expressed but are methylated in cell types where they are not expressed. Moreover, tumor cell DNA is frequently methylated to a different extent and in different regions than is the DNA of normal cells. The present invention is used for identifying which regions of the genome are methylated or mutated in different cell types, including cancerous cell types. The present invention also is used for identifying whether a tissue sample has a methylation or mutation pattern which is normal or like that of known cancer cells. The present invention can be used to identify aberrant expression of known or unknown genes. Such aberrant expression may occur at an incorrect location or an incorrect time, i.e. tissue or developmental specificity is lost. Genes and genomic regions discovered according to the present invention are useful for identifying products, e.g. mRNA, protein or fragments thereof, which are aberrantly expressed.

BACKGROUND OF THE INVENTION

DNA is often methylated in normal mammalian cells. For example, DNA is methylated to determine whether a given gene will be expressed and whether the maternal or the paternal allele of that gene will be expressed. See Melissa Little et al., *Methylation and p16: Suppressing the Suppressor*, 1 NATURE MEDICINE 633 (1995). While methylation is known to occur at CpG sequences, only recent studies indicate that CpNpG sequences may be methylated. Susan J. Clark et al., *CpNpG Methylation in Mammalian Cells*, 10 NATURE GENETICS 20, 20 (1995). Methylation at CpG sites has been much more widely studied and is better understood.

Methylation occurs by enzymatic recognition of CpG and CpNpG sequences followed by placement of a methyl ($CH_3$) group on the fifth carbon atom of a cytosine base. The enzyme that mediates methylation of CpG dinucleotides, 5-cytosine methyltransferase, is essential for embryonic development—without it embryos die soon after gastrulation. It is not yet clear whether this enzyme methylates CpNpG sites. Peter W. Laird et al., *DNA Methylation and Cancer*, 3 HUMAN MOLECULAR GENETICS 1487, 1488 (1994).

When a gene has many methylated cytosines it is less likely to be expressed. K. Willson, 7 TRENDS GENET. 107–109 (1991). Hence, if a maternally-inherited gene is more highly methylated than the paternally-inherited gene, the paternally-inherited gene will generally give rise to more gene product. Similarly, when a gene is expressed in a tissue-specific manner, that gene will often be unmethylated in the tissues where it is active, but will be highly methylated in the tissues where it is inactive. Incorrect methylation is thought to be the cause of some diseases including Beckwith-Wiedemann syndrome and Prader-Willi syndrome. I. Henry et al., 351 NATURE 665, 667 (1991); R. D. Nicholls et al., 342 NATURE 281, 281–85 (1989).

The methylation patterns of DNA from tumor cells are generally different than those of normal cells. Laird et al., supra. Tumor cell DNA is generally undermethylated relative to normal cell DNA, but selected regions of the tumor cell genome may be more highly methylated than the same regions of a normal cell's genome. Hence, detection of altered methylation patterns in the DNA of a tissue sample is an indication that the tissue is cancerous. For example, the gene for Insulin-Like Growth Factor 2 (IGF2) is hypomethylated in a number of cancerous tissues, such as Wilm's Tumors, rhabdomyosarcoma, lung cancer and hepatoblastomas. Rainner et al. 362 NATURE 747–49 (1993); Ogawa, et al., 362 NATURE 749–51 (1993); S. Zhan et al., 94 J. CLIN. INVEST. 445–48 (1994); P. V. Pedone et al., 3 HUM. MOL. GENET. 1117–21 (1994); H. Suzuki et al., 7 NATURE GENET 432–38 (1994); S. Rainier et al., 55 CANCER RES. 1836–38 (1995).

The present invention is directed to a method of detecting differential methylation at CpNpG sequences by cutting test and control DNAs with a restriction enzyme that will not cut methylated DNA, and then detecting the difference in size of the resulting restriction fragments.

While methylation-sensitive restriction enzymes have been used for observing differential methylation in various cells, no commercial assays exist for use on human samples because differentially methylated sequences represent such a minute proportion of the human genome that they are not readily detected. The human genome is both highly complex, in that it contains a great diversity of DNA sequences, and highly repetitive, in that it contains a lot of DNA with very similar or identical sequences. The high complexity and repetitiveness of human DNA confounds efforts at detecting and isolating the minute amount of differentially methylated DNA which may be present in a test sample. The present invention remedies this detection problem by providing new procedures for screening a selected subset of the mammalian genome which is most likely to contain genetic functions.

The present invention provides techniques for detecting and isolating differentially methylated or mutated segments of DNA which may be present in a tissue sample in only minute amounts by using one or more rounds of DNA amplification coupled with subtractive hybridization to identify such segments of DNA. DNA amplification has been coupled with subtractive hybridization in the Representational Difference Analysis (RDA) procedures disclosed in U.S. Pat. No. 5,436,142 to Wigler et al. and Nikolai Lisitsyn et al., *Cloning the Differences Between Two Complex Genomes*, 259 SCIENCE 946 (1993). However, for the subtractive hybridization step of such RDA procedures to proceed in a reasonable time and with reasonable efficiency, only a subset of the genome can be examined. To accomplish this necessary reduction in the complexity of the sample DNA, Wigler et al. and Lisitsyn et al. disclose cutting DNA samples with restriction enzymes that cut infrequently and randomly. However, selection of enzymes which randomly cut the genome means that the portion of the genome which is examined is not enriched for any particular population of DNA fragments. Thus, when RDA is used, only a random subset of the human genome, which includes repetitive elements, noncoding regions and other sequences which are generally not of interest, can be tested in a single experiment.

In contrast, the present invention is directed to methods which use enzymes that cut frequently and that specifically cut CG-rich regions of the genome. These enzymes are chosen because CG-rich regions of the genome are not evenly distributed in the genome—instead, CG-rich regions are frequently found near genes, and particularly near the promoter regions of genes. This means that the proportion of the genome that is examined by the present methods will be enriched for genetically-encoded sequences as well as for regulatory sequences. Moreover, unlike the RDA method, the present methods selectively identify regions of the genome which are hypomethylated or hypermethylated by using enzymes which specifically cut non-methylated CG-rich sequences. The present invention therefore represents an improvement over RDA methods because of its ability to select DNA fragments which are likely to be near or to encode genetic functions.

SUMMARY OF THE INVENTION

The present invention provides probes and methods of detecting whether a CNG triplet is hypomethylated or hypermethylated in a genomic DNA present in a test sample of cell.

The present invention provides a method of detecting whether a CNG triplet is hypomethylated or hypermethylated in a genomic DNA present in a test sample of cells which includes:

a) isolating genomic DNA from a control sample of cells and a test sample of cells to generate a control-cell DNA and a test-cell DNA;

b) cleaving the control-cell DNA and the test-cell DNA with a master restriction enzyme to generate cleaved control-cell DNA and cleaved test-cell DNA;

c) preparing a probe from a DNA isolated by the present methods, for example, a DNA selected from the group consisting of SEQ ID NO:7–10;

d) hybridizing the probe to the cleaved control-cell DNA and the cleaved test-cell DNA to form a control-hybridization complex and a test-hybridization complex; and e) observing whether the size of the control-hybridization complex is the same as the size of the test-hybridization complex;

wherein the master restriction enzyme cleaves a nonmethylated CNG DNA sequence but does not cleave a methylated CNG DNA sequence.

Similarly, the present invention provides a method of detecting whether a DNA site is mutated in a genomic DNA present in a test sample of cells which includes steps a) through e) above but where a detector restriction enzyme is used instead of the master restriction enzyme, wherein the detector restriction enzyme does not cleave a mutated DNA site but does cleave a corresponding nonmutated DNA site.

The present invention also provides methods of isolating probes to detect hypomethylation or hypermethylation in a CNG triplet of DNA. In particular, the present invention provides a method of isolating a probe to detect hypomethylation in a CNG triplet of DNA which includes:

a) cleaving a tester sample of genomic DNA with both a master restriction enzyme and a partner restriction enzyme to generate a cleaved tester sample;

b) ligating a first set of adaptors onto master enzyme cut DNA ends of the cleaved tester sample to generate a first-tester amplification template;

c) amplifying the first-tester amplification template to generate a first-tester amplicon by in vitro DNA amplification using primers that hybridize to the first set of adaptors;

d) cleaving off the first adaptors from the first-tester amplicon and ligating a second set of adaptors onto DNA ends of the first-tester amplicon to generate a second-adaptor-tester which has second adaptor ends;

e) melting and hybridizing the second-adaptor-tester with about a 10-fold to about a 10,000-fold molar excess of a driver DNA to generate a mixture of tester-tester product and tester-driver product;

f) adding nucleotides onto DNA ends present in the mixture to make a blunt-ended tester-tester product and a blunt-ended tester-driver product;

g) amplifying the blunt-ended tester-tester product and the blunt-ended tester-driver product by in vitro DNA amplification using primers that hybridize to second adaptor ends to generate a second-tester amplicon;

f) isolating a discrete DNA fragment from the second tester amplicon as a probe to detect the hypomethylation or the hypermethylation in a CNG triplet of DNA;

wherein the master restriction enzyme cleaves a nonmethylated CNG DNA sequence but does not cleave a methylated CNG DNA sequence;

wherein the partner restriction enzyme cleaves DNA to produce DNA fragments with a complexity of about 5% to about 25% of the genomic DNA in a size range which can be amplified by a DNA amplification enzyme; and wherein the driver DNA is cut with both the master restriction enzyme and the partner restriction enzyme and amplified using primers that recognize DNA ends cut by the master restriction enzyme.

Similarly, when the present invention provides a method of isolating a probe to detect hypermethylation in a CNG triplet of DNA, normal DNA is used instead of the tester DNA and the normal amplicon is annealed and hybridized with a molar excess of tester driver DNA.

Moreover the present methods are used to isolate probes to detect a mutation in a test sample of genomic DNA by using a detector enzyme instead of a partner restriction enzyme, wherein the detector restriction enzyme cleaves a normal DNA site but not a mutant DNA site.

The present invention further provides a kit for detecting hypomethylation in a CNG triplet of DNA which is present in a test tissue sample which includes a DNA or a probe isolated by the methods of the present invention, for example, a DNA having SEQ ID NO:7–10.

The present invention provides nucleic acid sequences which are differentially methylated in human breast and ovarian cancer tissues, as compared to normal tissue.

The present invention provides nucleic acid sequences which are useful as probes for determining the methylation state of genomic DNA sequences which are differentially methylated in tumor tissues.

Similarly, the present invention provides nucleic acid sequences which are useful as probes for the detection of mRNA expression, as well as oligonucleotide sequences which can be used to amplify and thus detect normal and aberrant expression of particular mRNA species.

The DNA sequences provided herein may also be expressed in host cells for the production of the encoded protein or protein fragments.

The proteins and protein fragments expressed from the nucleotide sequences disclosed herein are useful for the production of monoclonal antibodies. Such monoclonal antibodies have a variety of uses including, but not limited to, detection of normal or aberrant protein expression in human tissues and fluids.

BRIEF DESCRIPTIONS OF THE DRAWINGS

FIG. 1 provides a schematic diagram of how the MDD technique generally selects for DNA fragments which have non-methylated CG-rich ends. Driver DNA is isolated from a normal cell or tissue sample of the same tissue-type as the tester cell DNA. Tester DNA is isolated from a cell or tissue sample which likely has a mutation or a difference in the extent to which its DNA is methylated. Tester (FIG. 1a) and driver (FIG. 1b) DNAs are cleaved by the master (M) and partner (P) restriction enzymes. The master enzyme will not cleave DNA at sites that have a methyl group (superscript"m") but will cleave at sites which are non-methylated (superscript m having a line drawn through it). The partner enzyme cleaves the DNA into a size and a complexity appropriate for DNA amplification and subtractive hybridization. After cleavage, a small target fragment is completely excised from the tester DNA (FIG. 1b) but not from the driver DNA (FIG. 1b). Adaptors (m-linkers) which hybridize only to master-enzyme-cut DNA ends are ligated onto the tester and driver DNA fragments. Unique target DNAs from the tester sample will have adaptors on both ends. Upon DNA amplification using a primer that recognizes only the adaptor sequences, only DNA fragments with adaptors on both ends will be efficiently amplified.

Figure 2:
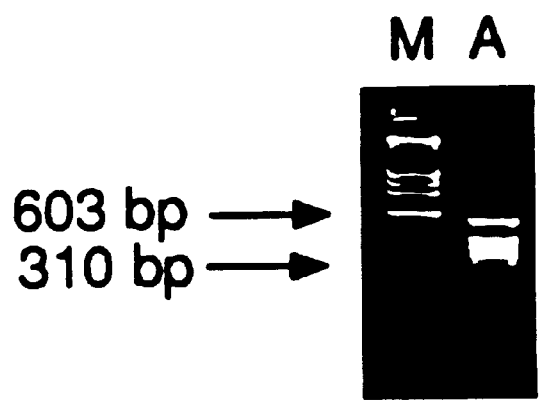

FIG. 2 depicts an agarose gel containing electrophoretically separated DNA fragments isolated by MDD from malignant B-cells derived from Chronic Lymphocytic Leukemia (CLL) patients. Lane A contains the different products isolated from CLL patient #111. Lane M contains Hae III 0174 DNA size markers. As illustrated, the present MDD methods give rise to discrete fragments of DNA which can readily be isolated and subcloned or used as probes for identifying the methylation patterns of genomic DNA samples from different cell types.

Figure 3:
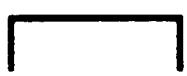
Figure 3:

FIG. 3 depicts a Southern blot of Msp I-digested tester (T) and driver (D) DNA hybridized with the CLL58 probe. The lane labeled "probe #58" contains a clone of the CLL58 probe. The lane labeled "T" contains amplified 2 $\mu$g CD5$^+$ B-cell DNA, whereas the lane "D" contains 2 $\mu$g amplified neutrophil DNA. Both T and D DNA samples were isolated from the CLL patient #111 and amplified by the MDD method. As a positive control, probe CLL58 hybridizes strongly to itself. Probe CLL58 also hybridizes strongly with the tester DNA but only weakly with the driver amplicon DNA—this is due to DNA hypomethylation in the tester DNA.

Figure 4:
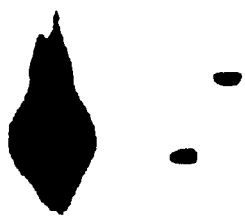

FIG. 4 depicts a Southern blot of Msp I-digested DNA hybridized with the CLL58 probe. The lane labeled "probe #58" contains a clone of the CLL58 probe. The lane labeled "T" contains 6 $\mu$g of CD5$^+$B-cell DNA, whereas lane "N" contains 6 $\mu$g of neutrophil DNA, each isolated from the CLL patient #111. As a positive control, probe CLL58 hybridizes strongly to itself. Probe CLL58 hybridizes with a lower band and several upper bands in B-cell DNA (lane T), while comparatively hybridizing much less with the lower band in neutrophil cell DNA (lane N). The lesser hybridization to the lower band in neutrophil DNA is due to DNA methylation which prevents complete excision of that fragment. Hence, the CLL58 probe provides a comparative methyl-differential display in B-cells and neutrophil cells.

Figure 5:
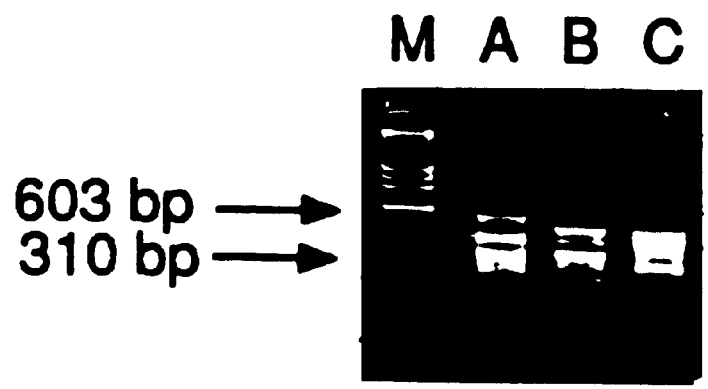

FIG. 5 depicts an agarose gel after electrophoresis of the different final products isolated from breast patient #13 (lane A), patient #14 (lane B) and breast patient #4 (lane C) using the MDD technique. Lane MW contains Hae III 0174 DNA size markers.

Figure 6A:
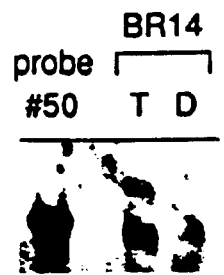

FIG. 6a depicts a Southern blot of Msp I-digested tester (T) and driver (D) DNA hybridized with the BR50 probe. The lane labeled "probe #50" contains a clone of the BR50 probe. The lane labeled "T" contains amplified breast tumor cell DNA, whereas the lane "D" contains amplified normal breast cell DNA. Both T and D DNA samples were isolated from the breast patient #14 and amplified by the MDD method. As a positive control, probe BR50 hybridizes strongly to itself. Probe BR50 also hybridizes strongly with the tester DNA but only weakly with the driver amplicon DNA—this is due to DNA hypomethylation in the tester DNA.

Figure 6B:

FIG. 6b depicts a Southern blot of Msp I-digested tester (T) and driver (D) DNA hybridized with the BR104 probe. The lane labeled "probe #104" contains a clone of the BR104 probe. The lane labeled "T" contains amplified breast tumor cell DNA, whereas the lane "D" contains amplified normal breast cell DNA. Both T and D DNA samples were isolated from the breast patient #13 and amplified by the MDD method. As a positive control, probe BR104 hybridizes strongly to itself. Probe BR104 also hybridizes strongly with the tester DNA but only weakly with the driver amplicon DNA—this is due to DNA hypomethylation in the tester DNA.

Figure 6C:
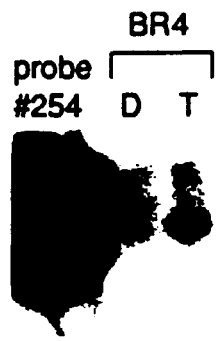

FIG. 6c depicts a Southern blot of Msp I-digested tester (T) and driver (D) DNA hybridized with the BR254 probe. The lane labeled "probe #254" contains a clone of the BR254 probe. The lane labeled "T" contains amplified breast tumor cell DNA, whereas the lane "D" contains amplified normal breast cell DNA. Both T and D DNA samples were isolated from the breast patient #4 and amplified by the MDD method. As a positive control, probe BR254 hybridizes strongly to itself. Probe BR254 also hybridizes strongly with the tester DNA but only weakly with the driver amplicon DNA—this is due to DNA hypomethylation in the tester DNA.

Figure 7A:
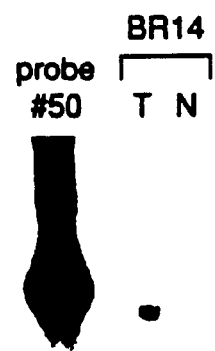

FIG. 7a depicts a genomic Southern blot of Msp I-digested DNA hybridized with a probe BR50 isolated from a breast cancer patient. The lane labeled "probe #50" contains a clone of the isolated BR50 probe. The lane labeled "T" contains 6 $\mu$g of B-cell DNA, whereas lane "N" contains 6 $\mu$g of normal breast DNA, each isolated from the breast cancer patient #14. As a positive control, probe BR50 hybridizes strongly to itself. Probe BR50 hybridizes strongly with a lower band and weakly with a medium band in breast tumor DNA (lane T). However, in normal breast cell DNA (lane N), probe BR50 hybridizes much less with the lower band and only weakly to an upper band. The lesser hybridization to the lower band in normal breast DNA is due to DNA methylation which prevents complete excision of that fragment. Hence, the BR50 probe provides a comparative methyl-differential display in tumor and normal breast cells.

Figure 7B:
Figure 7B:

FIG. 7b depicts a genomic Southern blot of Msp I-digested DNA hybridized with a probe BR104 isolated from a breast cancer patient. The lane labeled "probe #104" contains a clone of the isolated BR104 probe. The lane labeled "T" contains 6 $\mu$g of tumor DNA, whereas lane "N" contains 6 $\mu$g of normal breast cell DNA, each isolated from the breast cancer patient #13. As a positive control, probe BR104 hybridizes strongly to itself. Probe BR104 hybridizes strongly with a lower band and weakly with a medium band in tumor DNA (lane T). However, in normal breast cell DNA (lane N), probe BR104 hybridizes lightly with the lower band and moderately with middle and upper bands. The lesser hybridization to the lower band in normal breast DNA is due to DNA methylation which prevents complete excision of that fragment. Hence, the BR104 probe provides a comparative methyl-differential display in tumorous and normal breast cells.

Figure 7C:
Figure 7C:

FIG. 7c depicts a genomic Southern blot of Msp I-digested DNA hybridized with a probe BR254 isolated from a breast cancer patient. The lane labeled "probe #254" contains a clone of the isolated BR254 probe. The lane labeled "T" contains 6 µg of B-cell DNA, whereas lane "N" contains 6 µg of normal breast cell DNA, each isolated from the breast cancer patient #4. As a positive control, probe BR254 hybridizes strongly to itself. Probe BR254 hybridizes strongly with a lower band and with an upper band in tumor DNA (lane T). However, in normal breast cell DNA (lane N), probe BR254 hybridizes only with the upper band. The lack of hybridization to the lower band in normal breast DNA is due to DNA methylation which prevents excision of that fragment. Hence, the BR254 probe provides a comparative methyl-differential display in tumorous and normal breast cells.

Figure 8:
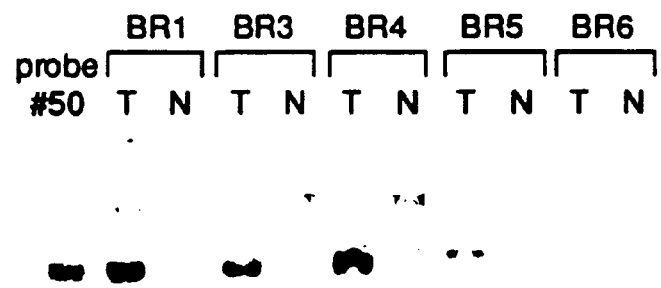

FIG. 8 depicts a Southern blot of Msp I-digested genomic DNA from five different breast cancer patients which was hybridized with the BR50 probe. The number for each patient is listed above the bracket. The hybridization patterns of tumor (T) and matched normal (N) DNAs from each patient are provided for comparison. The lane labeled "probe #50" contains a clone of the isolated BR50 probe. The lane labeled "T" contains 6 µg of DNA isolated from a tumor, whereas lane "N" contains 6 µg of DNA from normal breast tissue. As a positive control, probe BR50 hybridizes strongly to itself. For each of the five patients, probe BR50 hybridizes strongly with a lower band and less strongly with an upper band in the tumor DNA samples (T). However, probe BR50 hybridizes much less with the lower band in the normal DNA samples (N). The lesser hybridization to the lower band in normal DNA is due to DNA methylation which prevents complete excision of that fragment. Hence, the BR50 probe provides a comparative methyl-differential display in breast tumor and normal DNA samples.

Figure 9:
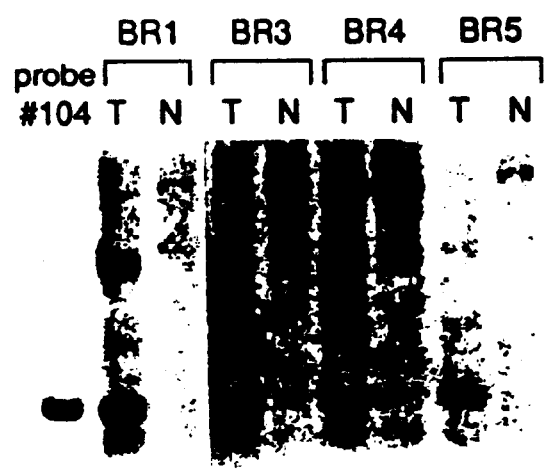

FIG. 9 depicts a Southern blot of Msp I-digested genomic DNA from four different breast cancer patients which was hybridized with the BR104 probe. The number for each patient is listed above the bracket. The hybridization patterns of tumor (T) and matched normal (N) DNAs from each patient are provided for comparison. The lane labeled "probe #104" contains a clone of the isolated BR104 probe. As a positive control, probe BR104 hybridizes strongly to itself. The lanes labeled "T" contain 6 µg of DNA isolated from a breast tumor, whereas the lanes labeled "N" contain 6 µg of DNA from normal breast tissue. For tumor DNA from each of the four patients, probe BR104 hybridizes with a lower band and a middle band. In the normal DNA, the probe hybridizes mainly with the middle band and an upper band. The lesser hybridization to the lower band in normal DNA is due to DNA methylation which prevents complete excision of that fragment. Hence, the BR104 probe provides a comparative methyl-differential display in breast tumor and normal breast DNA samples.

Figure 10:
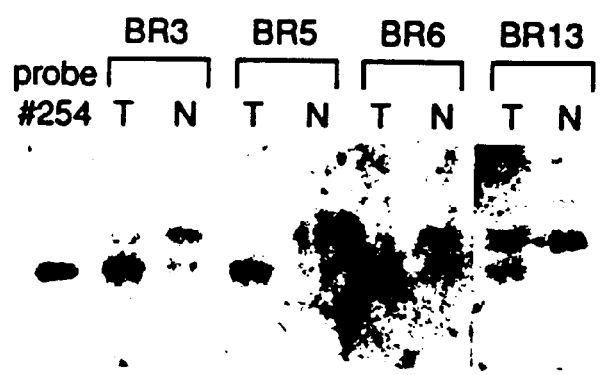

FIG. 10 depicts a Southern blot of Msp I-digested genomic DNA from four different breast cancer patients which was hybridized with the BR254 probe. The number for each patient is listed above the bracket. The hybridization patterns of tumor (T) and matched normal (N) DNAs from each patient are provided for comparison. The lane labeled "probe #254" contains a clone of the isolated BR254 probe. The lane labeled "T" contains 6 µg of DNA isolated from a breast tumor, whereas lane "N" contains 6 µg of DNA from normal breast tissue. As a positive control, probe BR254 hybridizes strongly to itself. For each of the four patients, probe BR254 hybridizes strongly with a lower band and less strongly with an upper band in the tumor DNA samples (T). However, probe BR254 hybridizes much less with the lower band in the normal DNA samples (N). The lesser hybridization to the lower band in normal DNA is due to DNA methylation which prevents complete excision of that fragment. Hence, the BR254 probe provides a comparative methyl-differential display in breast tumor and normal DNA samples.

Figure 11:
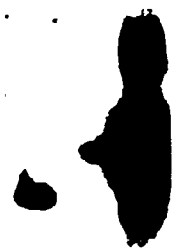

FIG. 11 depicts an amplification pattern detected by probe BR254 in DNA isolated from a breast tumor biopsy. FIG. 11 provides a Southern blot of normal (N) and tumor (T) DNA from breast cancer patient #23 which was digested with Msp I and hybridized with the BR254 probe. Both the N and T lanes contain 6 µg of DNA. The lane labeled "probe #254" contains a clone of the isolated BR254 probe, which hybridizes to itself. In the tumor DNA, the BR254 probe hybridizes very, very strongly to a DNA fragment to which it hybridizes only moderately in normal DNA. This indicates that the breast tumor DNA of patient #23 has a highly amplified region of genomic DNA which is not present in her normal DNA.

Figure 12:
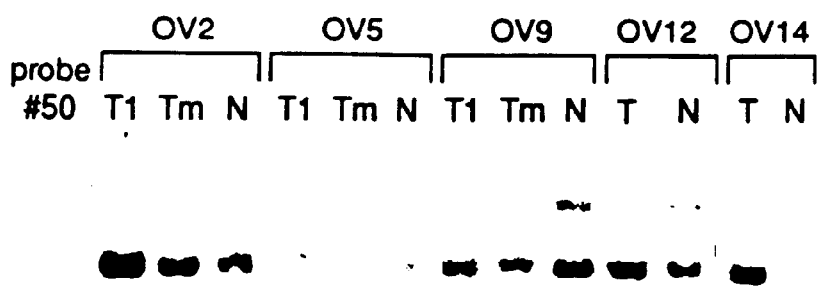

FIG. 12 depicts a Southern blot of Msp I-digested genomic DNA from five different ovarian cancer patients which was hybridized with the BR50 probe. The number for each patient is listed above the bracket. The hybridization patterns of 6 µg primary tumor DNA (T or T1), 6 µg metastatic tumor DNA (Tm) and 6 µg normal ovarian DNA (N) from these patients are provided for comparison. The lane labeled "probe #50" contains a clone of the isolated BR50 probe. The lane labeled "T " contains 6 µg of DNA isolated from a ovarian tumor, whereas lane "N" contains 6 µg of DNA from normal ovarian tissue. As a positive control, probe BR50 hybridizes strongly to itself. In primary tumor DNAs, the probe predominantly hybridizes with the lower bands, and slightly hybridizes with the upper bands. In metastatic tumor DNAs, the probe only hybridizes with the lower bands. In normal DNAs, the probe hybridized with the lower bands and the upper bands. The lesser hybridization to the lower band in normal DNA is due to DNA methylation which prevents complete excision of that fragment. Hence, the BR50 probe provides a comparative methyl-differential display in ovarian tumor and normal DNA samples. The degree of DNA hypomethylation may be related to the progress of the disease.

Figure 13:
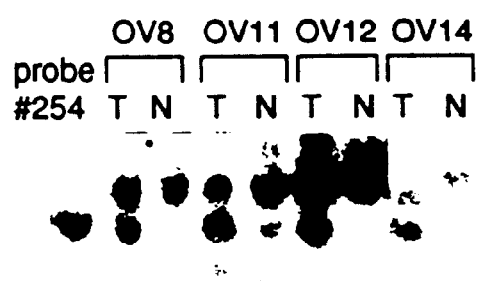

FIG. 13 depicts a Southern blot of Msp I-digested genomic DNA from four different ovarian cancer patients which was hybridized with the BR254 probe. The number for each patient is listed above the bracket. The hybridization patterns of tumor (T) and matched normal (N) DNAs from each patient are provided for comparison. The lane labeled "probe #254" contains a clone of the isolated BR254 probe. The lane labeled "T" contains 6 µg of DNA isolated from a ovarian tumor, whereas lane "N" contains 6 µg of DNA from normal ovarian tissue. As a positive control, probe BR254 hybridizes strongly to itself. For each of the four patients, probe BR254 hybridizes with a lower band and with an upper band in the tumor DNA samples (T). However, probe BR254 hybridizes only with the upper band in the normal DNA samples (N). The lack of hybridization to the lower band in normal DNA is due to DNA methylation which prevents excision of that fragment. Hence, the BR254 probe provides a comparative methyl-differential display in ovarian tumor and normal DNA samples.

Figure 14:
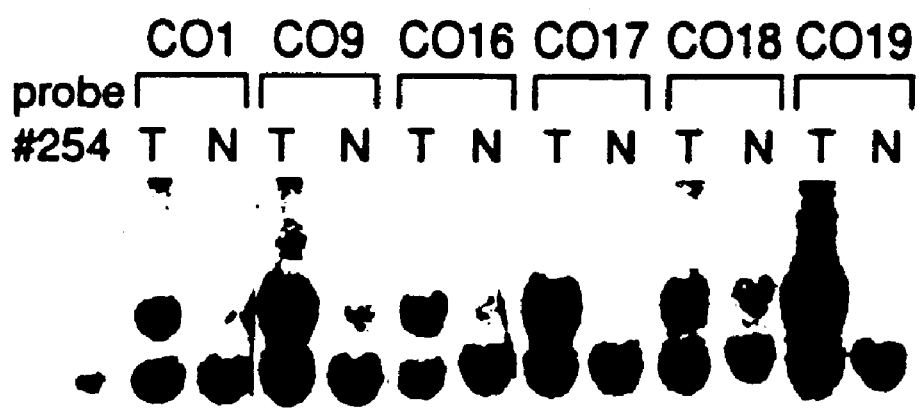

FIG. 14 depicts a Southern blot of Msp I-digested genomic DNA from six different colon cancer patients which was hybridized with the BR254 probe. The number for each patient is listed above the bracket. The hybridization patterns of 6 µg tumor (T) and 6 µg matched normal (N)

DNAs from each patient are provided for comparison. The lane labeled "probe #254" contains a clone of the isolated BR254 probe as a positive control to show that probe BR254 hybridizes strongly to itself. In the tumor DNA, the probe hybridizes with lower and upper bands with equal intensity. In the normal DNA, the probe hybridizes mainly with the lower band. Hence, the BR254 probe detects alteration of DNA methylation in colon cancer DNA.

Figure 15:
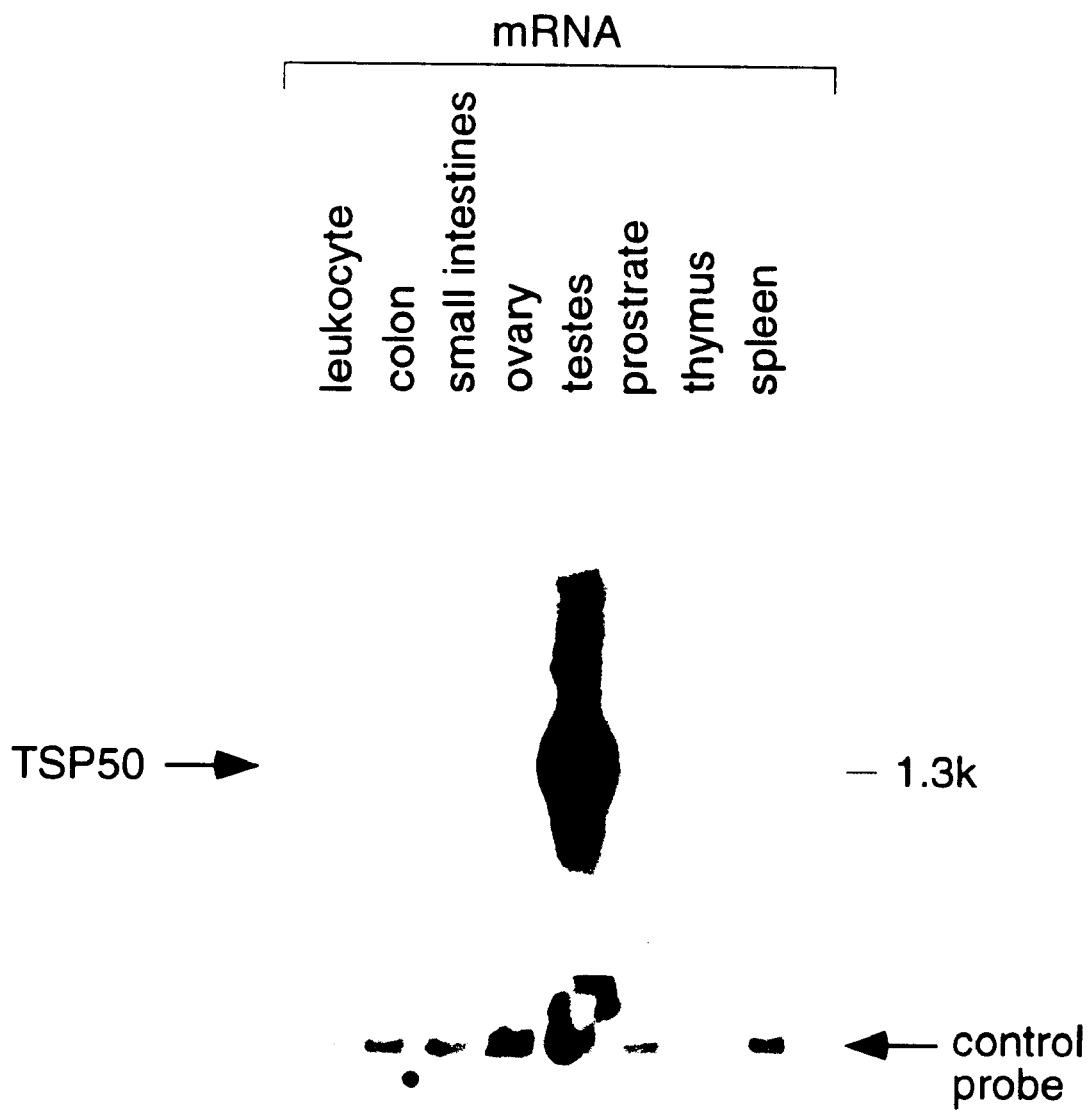

FIG. 15 depicts a Northern blot of mRNA samples from several normal human tissues, which was hybridized with probe BR50. For quantitative comparison, the same membrane was hybridized to a control probe which is expressed in all tissues. As indicated by the band labeled "TSP50", probe BR50 hybridizes strongly with testes specific mRNA, but not with mRNA from other sources.

DETAILED DESCRIPTION OF THE INVENTION

The present invention provides methods and probes for detecting and isolating DNA sequences which are mutated or methylated in one tissue type but not in another. These methods are herein named Methyl- (or Mutant-) Differential Display ("MDD") methods. These MDD methods, and probes that are isolated by MDD, are useful inter alia for identifying genes that are expressed in a tissue-specific manner. Moreover, the present MDD methods and probes are useful for detecting cancerous cells, viruses, bacteria, point mutations, amplifications, deletions and genomic rearrangements.

To detect whether a DNA sequence is differentially methylated, the present invention uses methylation-sensitive restriction enzymes to cleave tester and control DNAs. These methylation-sensitive restriction enzymes will cut their DNA recognition sites when those sites are not methylated but do not cut the DNA site if it is methylated. Hence, a non-methylated tester DNA will be cut into smaller sizes than a methylated control DNA. Similarly, a hypermethylated tester DNA will not be cleaved and will give rise to larger fragments than a normally non-methylated control DNA.

The present invention is particularly useful for detecting and isolating DNA fragments that are normally methylated but which, for some reason, are non-methylated in a small proportion of cells. Such DNA fragments may normally be methylated for a number of reasons. For example, such DNA fragments may be normally methylated because they contain, or are associated with, genes that are rarely expressed, genes that are expressed only during early development, genes that are expressed in only certain cell-types, and the like.

While highly expressed genes are frequently unmethylated, those highly expressed genes are often not very interesting because they are "housekeeping genes" which contribute to generalized cellular functions and cellular survival, rather than to the determination of what makes one cell-type different from another. Moreover, highly expressed genes have generally already been isolated and characterized.

Unlike the housekeeping genes, non-methylated but normally-methylated, DNA fragments are present in just a small proportion of cells. Therefore, it is very difficult to detect or isolate those fragments and to distinguish them from non-methylated housekeeping genes. The present invention solves this problem by using a combination of DNA amplification and hybridization/subtraction techniques. The amplification steps enrich the genomic DNA sample with small DNA fragments that have both 5' and 3' ends cut by the methylation-sensitive enzyme. The hybridization/subtraction steps eliminate fragments encoding non-methylated housekeeping genes and fragments which are cut on only one end by the methylation-sensitive enzyme. Several rounds of amplification and hybridization/subtraction can be used if a discrete number of fragments are not isolated with the first round.

The fragments isolated by MDD are cut on both ends by the methylation-sensitive master enzyme because only fragments cut on both ends with the master enzyme are efficiently amplified. This is accomplished by using primers during DNA amplification that recognize only the master-enzyme-cut DNA ends. Such primer specificity is created by adding adaptors to the DNA ends of a sample cut with both the master enzyme and a partner restriction enzyme. The adaptors have unique sequences which hybridize with the DNA amplification primers. The partner enzyme is used to generate a mixture of DNA fragments of an appropriate size and complexity for DNA amplification but also creates a population of DNA molecules which will not accept the adaptors because they have partner-enzyme-cut ends.

Similarly, for detecting and isolating fragments which contain a mutation, DNA fragments are cut with a master enzyme and a partner (detector) enzyme, where the partner (detector) enzyme may cut normal DNA but which will not cut mutated DNA. The master enzyme normally used for MDD is a methylation-sensitive enzyme which recognizes and cuts CG-rich sites in genomic DNA. However, for detecting and isolating fragments that contain a mutation, nonmethylation sensitive master enzymes can also be used. Any restriction enzyme can be used as a master restriction enzyme for detecting and isolating mutations so long as it cuts at a different sequence than the detector enzyme. However, a master enzyme which cuts in CG-rich regions is preferred because it selects for regions associated with genes while the detector enzyme identifies and permits isolation of the mutation by cutting only the nonmutant DNA fragments To confirm whether fragments isolated by the present MDD methods can detect differentially methylated or mutated DNA sites, they are tested as probes on genomic DNAs which are cut with methylation-sensitive or mutant-detector enzymes, respectively. If the probe detects a different size fragment in DNA which is known, or suspected to be, hypomethylated, hypermethylated or mutated than in normal DNA, then the probe can detect differentially methylated or mutated DNA sites.

DNA fragments isolated by the present methods can therefore constitute probes, for example, for detecting hypomethylation, hypermethylation or mutation in DNA fragments which are normally methylated.

In particular, the present invention provides a method of isolating probes to detect hypomethylation in a CNG triplet of DNA which includes:

a) cleaving a tester sample of genomic DNA with a master restriction enzyme and a partner restriction enzyme to generate a cleaved tester sample;

b) amplifying the cleaved tester sample using primers that recognize DNA ends cut by the master restriction enzyme, to generate a first tester amplicon;

c) melting and hybridizing the first test amplicon with a driver DNA to generate a tester-tester product and a tester-driver product;

d) adding nucleotides to the ends of the tester-tester product and the tester-driver product to make a blunt-ended tester-tester product and a blunt-ended tester-driver product;

e) amplifying the blunt-ended tester-tester product and the blunt-ended tester-driver product by using primers which recognize only master-enzyme-cut DNA ends, to produce a second tester amplicon;

f) isolating a discrete DNA fragment from the second tester amplicon as a probe to detect hypomethylation a CNG triplet of DNA;

wherein the master restriction enzyme cleaves a nonmethylated CNG DNA sequence but does not cleave a methylated CNG DNA sequence;

wherein the partner restriction enzyme cleaves DNA to produce DNA fragments with a complexity of about 5% to about 25% of the genomic DNA in a size range which can be amplified by a DNA amplification enzyme; and wherein the driver DNA is cut with both the master restriction enzyme and the partner restriction enzyme, and then amplified by using primers that recognize DNA ends cut by the master restriction enzyme.

In another embodiment, the master-enzyme-cutDNA ends are distinguished from the partner-enzyme-cutDNA ends by ligating a first set of adaptors onto master-enzyme-cut DNA ends of the cleaved tester sample to generate a first-tester amplification template. This first-tester amplification template is then amplified to generate a first-tester amplicon by in vitro DNA amplification using primers that hybridize to the first set of adaptors. Hence, only DNA fragments which were cut by the master restriction enzyme will be amplified. The first adaptors are then cleaved off the first-tester amplicon and a second set of adaptors is ligated onto master-enzyme-cut DNA ends of the first-tester amplicon to generate a second-adaptor-tester which has second adaptor ends. As before, this tester DNA is melted and hybridized with a large molar excess of a driver DNA to generate a mixture of tester-tester product and tester-driver product. The DNA ends of these products are made blunt by adding nucleotides and the blunt-ended tester-driver product is amplified the blunt-ended tester-tester product and the blunt-ended tester-driver product by in vitro DNA amplification using primers that hybridize to second adaptor ends. This generates a second-tester amplicon from which a discrete DNA fragments can be isolated as probes to detect the hypomethylation in a CNG triplet of DNA.

As used herein, hypomethylation means that at least one cytosine in a CG or CNG di- or tri-nucleotide site in genomic DNA of a given cell-type does not contain $CH_3$ at the fifth position of the cytosine base. Cell types which may have hypomethylated CGs or CCGs include any cell type which may be expressing a non-housekeeping function. This includes both normal cells that express tissue-specific or cell-type specific genetic functions, as well as tumorous, cancerous, and similar cell types. Cancerous cell types and conditions which can be analyzed, diagnosed or used to obtain probes by the present methods include Wilm's cancer, breast cancer, ovarian cancer, colon cancer, kidney cell cancer, liver cell cancer, lung cancer, leukemia, rhabdomyosarcoma, sarcoma, and hepatoblastoma.

Genomic DNA samples can be obtained from any mammalian body fluid, secretion, cell-type, or tissue, as well as any cultured cell or tissue.

The present MDD technique involves preparation of a driver DNA and a tester DNA. A driver DNA is genomic DNA from a "normal" cell type. A tester DNA is genomic DNA from a "test" cell type which may have mutated DNA sites, hypermethylated DNA sites or non-methylated DNA sites in place of the normal DNA at that site. Such normal cell types are cells of the same tissue-type as the "test" cell type, but which are normally methylated and are not mutated. Test cell types include cells that express tissue or cell-specific functions, cancer cells, tumor cells and the like. For example, if breast cancer cells are selected as the test cell type, the normal cell type would be breast cells that are not diseased or cancerous. Preferably, test and normal cell types are isolated from the same person.

After isolation, the tester DNA and the driver DNA are separately cut with both the master and partner restriction enzymes. As provided by the present invention, the master restriction enzyme cleaves a CNG DNA sequence. The master restriction enzyme produces sticky ends, rather than blunt ends, when it cuts. In general, the master enzyme used in the present methods cleaves only non-methylated CNG DNA sequences and does not cleave methylated CNG DNA sequences. However, for selected applications a non-methylation sensitive master enzyme can be used, for example, for detecting and isolating mutations. For detecting and isolating hypomethylated DNA sites, a methylation-sensitive master enzyme should be used, for example, the Msp I restriction enzyme which recognizes and cleaves DNA at nonmethylated CCGG but will not cleave the CCGG sequence when the outer cytosine is methylated. Master restriction enzymes contemplated by the present invention include Msp I, BsiS I, Hin2 I and the like. In a preferred embodiment, Msp I is used as the master restriction enzyme for detecting and isolating a DNA fragment containing a hypomethylated site.

According to the present invention, a partner restriction enzyme cleaves DNA to produce DNA fragments with a complexity of about 5% to about 25% of the genomic DNA in a size range which can be amplified by a DNA amplification enzyme. As used herein, the complexity of mixture of DNA fragments is the number of different DNA fragments within a selected size range. When mammalian DNA is used, the present methods can effectively screen a DNA sample containing about 1% to about 25% of the mammalian genome. In a preferred embodiment, a DNA sample has about 5% to about 15% of the total DNA sequences in the mammalian genome. In an especially preferred embodiment, the DNA sample has about 10% of the total DNA sequences in the mammalian genome.

According to the present invention, the size range of DNA fragments in a sample of genomic DNA is that size range which can be amplified by in vitro DNA amplification. When polymerase chain reaction ("PCR") is used, that size range is about 2000 base pairs (bp) to about 75 bp. Preferably the selected size range is about 1500 bp to about 100 bp. More preferably the selected size is about 1000 bp to about 150 bp.

As used herein, the preferred size is generated by the action of both the master and partner restriction enzymes. Hence, if the partner restriction enzyme generates a population of genomic DNA fragments which are about 1000 bp or smaller, but, in combination with the master restriction enzyme a population of fragments which are less than 50 bp is generated, a different set of partner and master enzymes is preferably used.

Also according to the present invention, the partner restriction enzyme cleaves DNA to produce ends that are neither homologous nor complementary to a sticky end produced by the master restriction enzyme.

Any convenient restriction enzyme is used as a partner restriction enzyme to identify CNG sites that are hypomethylated, so long as the appropriate complexity and size of DNA fragments are generated. For convenience, a partner restriction enzyme that operates under the same conditions as the master restriction enzyme may be used. For example, Mse I is a good partner restriction enzyme which can be used under the same conditions as the preferred Msp I master restriction enzyme. When the preferred Msp I master restriction enzyme is used, the partner restriction enzyme preferably recognizes and cuts a 4-nucleotide sequence. Moreover, in a preferred embodiment, the partner restriction enzyme cuts an AT-rich site or generates a blunt end to avoid any ligation of adaptors, which are designed to attach to master enzyme cut ends, onto the ends generated by the partner enzyme. Preferred partner restriction enzymes include Mse I, Sau3 A, Rsa I, TspE I, Mae I, Nia III, Dpn I and the like.

Cleavage methods and procedures for selecting restriction enzymes for cutting DNA at specific sites are known to the skilled artisan. For example, many suppliers of restriction enzymes provide information on conditions and types of DNA sequences cut by specific restriction enzymes, including New England BioLabs, ProMega Biochem, Boehringer-Mannheim and the like. Sambrook et al. provide a general description of methods for using restriction enzymes and other enzymes. See Sambrook et al., 1989 *Molecular Cloning: A Laboratory Manual*, Vols. 1–3 (Cold Spring Harbor Press, Cold Spring Harbor, N.Y.).

After cleaving the DNA with the master and partner restriction enzymes, a set of adaptors is hybridized and ligated onto the sticky DNA ends produced by the master restriction enzyme. The adapters are selected so that they will ligate to the CG-rich ends of the DNA cut by the master restriction enzyme but not to the ends of the fragments that were cut with the partner restriction enzyme. Because only the DNA ends of fragments in the tester and driver genomic DNA samples will be single-stranded, adaptors need not be longer than about 12 nucleotides to specifically recognize and hybridize to the master enzyme-cut ends. However, the adaptors are chosen not only to ligate to DNA ends cut by the master restriction enzyme, but also to be a good size and DNA sequence to act as recognition sites for primers used during DNA amplification. Adaptors are chosen so that, when the mixture of master and partner enzyme cut DNA fragments is amplified using primers that hybridize to those adaptors, only those fragments that have the adaptor and thus were cut with the master restriction enzyme will be amplified. Hence, after hybridization and ligation the adaptor ends should have a unique sequence and be of sufficient length to be a unique recognition site for primers selected for in vitro DNA amplification.

Preferred sets of adaptors of the present invention include those of SEQ ID NO: 1–6. As used herein:

the MSA24 adaptor has SEQ ID NO:1— CTCGTCGTCAGGTCAGTGCTTCAC the MSA12 adaptor has SEQ ID NO:2— CGGTGAAGCACT the MSB24 adaptor has SEQ ID NO:3— TAGAGCCACGTAGCTGCTGTAGTC the MSB12 adaptor has SEQ ID NO:4— CGGACTACAGCA the MSC24 adaptor has SEQ ID NO:5— ACCGTGGACTGGATAGGTTCAGAC and the MSC12 adaptor has SEQ ID NO:6— CGGTCTGAACCT.

In one embodiment, the SEQ ID NOS:1 and 2 (MSA24 and MSA12) adaptors are single-stranded and are used as the first set of adaptors. These single-stranded adaptors are annealed and hybridized onto DNA ends cut with the master restriction enzyme and then ligated to those DNA ends by incubation with ligase. Both the tester and driver DNAs receive the first set of adaptors. Thus, the master-cut ends of both the tester and driver DNAs will have adaptors while DNA ends cut with the partner enzyme, from either the tester or driver, will have no such adaptors.

The tester and driver samples are then separately amplified by known DNA amplification procedures using primers that hybridize to the adaptors. For example, when the SEQ ID NO:1 and 2 adaptors are used, an oligonucleotide having SEQ ID NO:1 can be used as a primer for DNA amplification of only the master enzyme cut DNA fragments. Such DNA amplification generates a tester amplicon and a driver amplicon. In both the tester and driver amplicons, only fragments which are cut with the master restriction enzyme will be amplified.

DNA amplification procedures for use in the present MDD methods include any in vitro amplification procedure which provides sequence-specific synthesis of a nucleic acid fragment relative to the complex bulk of nucleic acid present in a sample. The specificity of the process is determined by enzymatic recognition of a specific sequence or by the oligonucleotide primers which are capable of hybridizing only with selected adaptors that are added onto the ends of master restriction cut DNA fragments.

In vitro DNA amplification techniques are known in the art. A review of such techniques can be found in Kwoh et al., 8 *Am. Biotechnol. Lab.* 14 (1990). In vitro nucleic acid amplification techniques include polymerase chain reaction (PCR), transcription-based amplification system (TAS), self-sustained sequence replication system (3SR), ligation amplification reaction (LAR), ligase-based amplification system (LAS), Qβ RNA replication system and run-off transcription.

PCR is a preferred method for DNA amplification. PCR synthesis of DNA fragments occurs by repeated cycles of heat denaturation of DNA fragments, primer annealing onto the adaptor ends of the master-cut DNA fragment, and primer extension. These cycles can be performed manually or, preferably, automatically. Thermal cyclers such as the Perkin-Elmer Cetus cycler are specifically designed for automating the PCR process, and are preferred. The number of cycles per round of synthesis can be varied from 2 to more than 50, and is readily determined by considering the source and amount of the nucleic acid template, the desired yield and the procedure for detection of the synthesized DNA fragment.

PCR techniques and many variations of PCR are known. Basic PCR techniques are described by Saiki et al. (1988 *Science* 239:487–491) and by U.S. Pat. Nos. 4,683,195, 4,683,202 and 4,800,159, which are incorporated herein by reference.

The conditions generally required for PCR include temperature, salt, cation, pH and related conditions needed for efficient copying of the master-cut fragment. PCR conditions include repeated cycles of heat denaturation (i.e. heating to at least about 95° C.) and incubation at a temperature permitting primer: adaptor hybridization and copying of the master-cut DNA fragment by the amplification enzyme. Heat stable amplification enzymes like the pwo, *Thermus aquaticus* or *Thermococcus litoralis* DNA polymerases are commercially available which eliminate the need to add enzyme after each denaturation cycle. The salt, cation, pH and related factors needed for enzymatic amplification activity are available from commercial manufacturers of amplification enzymes.

As provided herein an amplification enzyme is any enzyme which can be used for in vitro nucleic acid amplification, e.g. by the above-described procedures. Such amplification enzymes include pwo, *Escherichia coli* DNA polymerase I, Klenow fragment of *E. coli* DNA polymerase I, T4 DNA polymerase, T7 DNA polymerase, *Thermus aquaticus* (Taq) DNA polymerase, *Thermococcus litoralis* DNA polymerase, SP6 RNA polymerase, T7 RNA polymerase, T3 RNA polymerase, T4 polynucleotide kinase, Avian Myeloblastosis Virus reverse transcriptase, Moloney Murine Leukemia Virus reverse transcriptase, T4 DNA ligase, *E. coli* DNA ligase or Qβ replicase. Preferred amplification enzymes are the pwo and Taq polymerases. The pwo enzyme is especially preferred because of its fidelity in replicating DNA.

The length of the primers for use in MDD depends on several factors including the nucleotide sequence and the temperature at which these nucleic acids are hybridized or used during in vitro nucleic acid amplification. The considerations necessary to determine a preferred length for an oligonucleotide primer are well known to the skilled artisan. For example, as is known to the skilled artisan, the length of a short nucleic acid or oligonucleotide can relate to its hybridization specificity or selectivity. Because the tester and driver samples contain a complex mixtures of nucleic acids, primers which are shorter than about 12 nucleotides may hybridize to more than one site in the test genomic DNA, and accordingly would not have sufficient hybridization selectivity for amplifing only the master-cut fragments. However, a 12- to 15-nucleotide sequence is generally represented only once in a mammalian genome (Sambrook et al. 1989 *Molecular Cloning: A Laboratory Manual*, Vol. 2, Cold Spring Harbor Press, Cold Spring Harbor, N.Y.; pp. 11.7–11.8). Accordingly, to eliminate amplification of fragments which do not have adaptors, primers are chosen which are generally at least about 14 nucleotides long.

Preferably, the present primers are at least 16 nucleotides in length. More preferred primers are at least 17 nucleotides in length (Sambrook et al., pp. 11.7–11.8).

After amplification, the first set of adaptors are removed from the ends of the tester and driver amplicons by cleavage with the master restriction enzyme. Cleavage with the master restriction enzyme preserves the original ends of the fragments and removes all DNA which was not present in the tester DNA as originally isolated.

A second set of adaptors are ligated to the tester amplicon, but not to the driver amplicon. This generates a second-adaptor-tester sample. The second set of adaptors is selected so that they do not have the same sequence as the first set of adaptors and so that they hybridize, and hence ligate, only to DNA ends cut by the master restriction enzyme. The second set of adaptors should also form a good recognition site for primers which are used during DNA amplification.

During DNA amplification, non-methylated DNA fragments which are normally present in all cell types, and which may not be of interest, will also be amplified because they will have adaptors on their ends. At least one round of subtraction/hybridization followed by DNA amplification is used by the present MDD methods to remove these nonmethylated DNA fragments which likely encode "housekeeping" functions.

In general, the present MDD techniques remove "housekeeping" sequences by hybridizing the amplified tester DNA with a large molar excess of amplified driver DNA and amplifying only the tester-tester hybrids which have perfectly hybridized ends because those perfectly hybridized ends are the only sites recognized by the primers used for DNA amplification.

In particular, the amplified tester DNA (called the first test amplicon or the second-adaptor-tester)is mixed with a large molar excess of amplified driver DNA. The mixture is denatured, then renatured. As used herein, a large molar excess of driver to tester DNA is about a 10-fold to about a 10,000-fold molar excess of driver DNA to tester DNA. In a preferred embodiment the tester DNA is melted and hybridized with about a 10-fold to about a 1000-fold molar excess of a driver DNA. In a more preferred embodiment, the tester DNA is melted and hybridized with about a 100-fold molar excess of a driver DNA. Stringent hybridization conditions are preferably used during renaturation to maximize the formation of fragments with few mismatches.

The skilled artisan can vary the hybridization conditions used during MDD to achieve optimal hybridization of unique tester DNA fragments to their tester homolog. Conditions for achieving optimal hybridization are known to the skilled artisan and generally include temperature and salt concentrations permitting selective hybridization between two highly homologous DNA fragments, e.g. stringent hybridization conditions. Stringent conditions permit little or no detectable hybridization between mismatched driver or tester fragments, that is between fragments that have dissimilar sequences, particularly at the ends. Hybridization techniques are described, for example, in Sambrook et al., 1989 *Molecular Cloning: A Laboratory Manual*, Vols. 1–3 (Cold Spring Harbor Press, Cold Spring Harbor, N.Y.).

The ends of the renatured fragments are then filled in using a DNA polymerase, e.g. Taq or pwo polymerase. Such a "filling in" reaction makes the DNA fragments blunt-ended but does not eliminate any internally mismatched or unhybridized regions. To eliminate such mismatched hybrids, the renatured fragments may be treated with a nuclease that will remove single-stranded regions and mismatched nucleotides in the renatured fragments. For example, S1 nuclease, mung bean nuclease and the like can be used to eliminate mismatched hybrids. The nuclease will also cleave off mismatched nucleotides at the ends of either the tester or the driver fragment. Hence, mismatched hybrids will have ends that do not contain second adaptor ends. Only the single-stranded tester fragments with second adaptor ends that faithfully hybridize to an exact tester homolog will end up with a second adaptor end.

The subtraction/hybridization mixture is then amplified by in vitro DNA amplification procedures using primers that hybridize to the second adaptor ends. Hence, only the tester DNA fragments with second adaptor ends are amplified. Any tester DNA which hybridized with driver DNA will not be amplified. A large excess of driver DNA is used to promote formation of hybrids that are commonly found in both the tester and driver samples. The result is a second tester amplicon with fragments which were uniquely unmethylated in the original tester DNA sample.

DNA fragments cut on only one end with the master restriction enzyme ("single master-cut fragments") are eliminated by the present invention is several ways. First, only one end of those fragments will ligate to an adaptor. This means that, during any amplification step, the single master-cut fragments will not be amplified as quickly as the "double master-cut fragments" which have adaptors at both ends. As is known to the skilled artisan, fragments which hybridize with amplification primers at both ends are amplified geometrically, while DNA fragments which hybridize with amplification primers at only one end are amplified arithmetically. Second, during the subtraction/hybridization step those single master-cut fragments may also hybridize to their driver homologs because the driver is present in vast molar excess. This imperfect hybrid can be eliminated by treatment with nuclease, so it will not be amplified during the subsequent DNA amplification step.

Several rounds of amplification and subtraction/hybridization can be used to isolate discrete DNA fragments which can be used as probes to detect hypomethylation, hypermethylation and mutation in specific regions of the genome. Discrete DNA fragments isolated by the present MDD methods which can be used to detect hypomethylation, hypermethylation and mutations in genomic DNA samples from different cell types include DNA fragments having SEQ ID NO:7–10.

While discrete DNA fragments which detect hypomethylation also frequently detect hypermethylation, the MDD method is readily adapted to permit isolation of fragments which will specifically detect hypermethylation in identified sites of the genome. This is accomplished merely by using normal cell DNA as the source of DNA for the hypermethylation probe. In this case, the normally unmethylated DNA will be cut by the methylation-sensitive master enzyme while the hypermethylated test DNA will not be cut. To eliminate DNA fragments which are common to the normal and test DNA samples, the normal cell DNA is hybridized with an excess of test cell DNA (now called "test driver DNA"). Hence, isolation of hypermethylation probes generally involves the same manipulations, as used for isolation of hypomethylation probes, but the roles of the normal cell DNA and the test cell DNA are reversed.

Also for detecting and isolating DNA fragments that have a hypermethylated CNG, a methylation-sensitive enzyme can be used as a partner enzyme and a non-methylation sensitive enzyme as a master enzyme. When this modification is used, the adaptors are still designed to attach to the ends of DNA fragments cut by the non-methylation sensitive master restriction enzyme.

In particular, the present invention provides a method of isolating a probe to detect hypermethylation in a CNG triplet of DNA which includes:
 a) cleaving a normal sample of genomic DNA with a master restriction enzyme and a partner restriction enzyme to generate a cleaved normal sample;
 b) amplifying the cleaved normal sample using primers that recognize DNA ends cut by the master restriction enzyme, to generate a first normal amplicon;
 c) melting and hybridizing the first normal amplicon with a test driver DNA to generate a normal-normal product and a normal-driver product;
 d) adding nucleotides to the ends of the normal-normal product and the normal-driver product to make a blunt-ended normal-normal product and a blunt-ended normal-driver product;
 e) amplifying the blunt-ended normal-normal product and the blunt-ended normal-driver product by using primers which recognize only master-enzyme-cut DNA ends, to produce a second normal amplicon;
 f) isolating a discrete DNA fragment from the second normal amplicon as a probe to detect the hypermethylation in a CNG triplet of DNA;
 wherein the test driver DNA is cut with both the master restriction enzyme and the partner restriction enzyme, and then amplified by using primers that recognize DNA ends cut by the master restriction enzyme.

The normal sample of genomic DNA is obtained by isolating genomic DNA from a "normal" cell type, and the test driver DNA is obtained by isolating genomic DNA from a "test" cell type which may have hypermethylated DNA sites in place of the normal non-methylated DNA at that site. Here, the test cell type is a cancerous or tumorous cell type.

In a further embodiment, the present MDD techniques can be used to identify and isolate mutations in genomic DNA and it has particular utility for identifying mutations which are near the promoters or coding regions of genes. Nonmethylation-sensitive master restriction enzymes can be used for isolating mutations. However, the preferred master enzymes recognize CNG DNA sequences including CpG dinucleotides which are frequently methylated in human genome. Condensed CpG islands appear in gene promoter regions, or even in the first exons. Because CpG islands appear in gene promoter regions, and in the first few exons of many genes, MDD-identified lesions will often be close to genes which cause disease.

According to the present invention, MDD can be used to isolate probes for detecting any type of genomic lesion. For example, MDD can be used to identify fragments which have point mutations, deletions, insertions, amplifications, rearrangements, and other mutations.

MDD is readily adapted for isolating mutations in DNA sequence by using a partner enzyme, now called a detector enzyme, that cuts normal DNA but which will not cut the mutated DNA. For example, a point mutation in tester DNA can be identified when a cleavage site recognized by the detector enzyme is eliminated. When cut with master and detector restriction enzymes, a fragment with both ends cleaved by the master enzyme will be present in the tester DNA. However, the detector enzyme cleaves this fragment in the driver DNA, because normal DNA has no point mutation. As a result, the fragment containing the point mutation will be isolated after performing the present MDD amplification and subtraction/hybridization steps. The point mutation can be easily identified by comparing the DNA sequence of the isolated mutant fragment with the DNA sequence of the homolog isolated from a matched normal genomic DNA. Moreover, the mutant tester fragment will contain the entire mutation—rather than just part of the mutation as would occur if a detector enzyme were used that cut the mutation rather than the normal DNA site.

Similarly, MDD is readily adapted for isolating deletion mutations in DNA simply by using tester DNA as the driver DNA and normal DNA as the source of the intact fragment whose homolog in the tester DNA has a deletion. The deletion mutant fragment can be isolated by virtue of its partial homology with the normal DNA fragment.

In particular, the present invention provides a method of identifying a probe to detect a mutation in a tester sample of genomic DNA which includes:
 a) cleaving a tester sample of genomic DNA with both a master restriction enzyme and a detector restriction enzyme to generate a cleaved tester sample;
 b) ligating a first set of adaptors onto master enzyme cut DNA ends of the cleaved tester sample to generate a first-tester amplification template;
 c) amplifying the first-tester amplification template to generate a first-tester amplicon by in vitro DNA amplification using primers that hybridize to the first set of adaptors;
 d) cleaving off the first adaptors from the first-tester amplicon and ligating a second set of adaptors onto DNA ends of the first-tester amplicon to generate a second adaptor-tester which has second adaptor ends;
 e) melting and hybridizing the second-adaptor-tester with about a 10-fold to about a 10,000-fold molar excess of a driver DNA to generate a mixture of tester-tester product and tester-driver product;
 f) adding nucleotides onto DNA ends present in the mixture to make a blunt-ended tester-tester product and a blunt-ended tester-driver product;

g) amplifying the blunt-ended tester-tester product and the blunt-ended tester-driver product by in vitro DNA amplification using primers that hybridize to second adaptor ends to generate a second-tester amplicon;

h) isolating a discrete DNA fragment from the second tester amplicon as a probe to detect a mutation in the tester sample of genomic DNA;

wherein the detector restriction enzyme cleaves a normal DNA site but a mutant DNA site to produce DNA fragments with a complexity of about 5% to about 25% of the genomic DNA in a size range which can be amplified by a DNA amplification enzyme; and wherein the driver DNA is cut with both the master restriction enzyme and the detector restriction enzyme and amplified using primers that recognize DNA ends cut by the master restriction enzyme.

Probes isolated by the present MDD techniques have at least about 14 nucleotides to about 2000 nucleotides.

It is well known in the art to adjust hybridization and wash solution contents and temperatures such that stringent hybridization conditions are obtained. Preferred stringent conditions are those that allow a probe to hybridize to sequences which are more than 90% complementary to the probe and not to those which are less than 70% complementary. Stringency depends on such parameters as the size and nucleotide content of the probe being utilized. See Sambrook et al. and other sources for general descriptions and examples.

For identifying mutations and isolating DNA fragments containing those mutations, selection of a detector restriction enzyme involves identifying an enzyme which will not cut mutated genomic DNA but which will cut normal DNA. The skilled artisan can readily perform this analysis, for example, by testing a plurality of restriction enzymes in the present MDD methods.

According to the present invention, a mutation, hypomethylation and hypermethylation at a specific site in genomic DNA can be detected by observing whether the size or intensity of a DNA fragment cut with a master or detector restriction enzyme is the same in control and test samples. This can be done by cutting genomic DNA isolated from control and test tissue samples with the master or detector restriction enzyme, hybridizing a probe to the control and test DNAs and observing whether the two hybridization complexes are the same or different sizes or intensities.

In particular, the present invention provides a method of detecting whether a CNG triplet is hypomethylated or hypermethylated in a genomic DNA present in a test sample of cells which includes:

a) isolating genomic DNA from a control sample of cells and a test sample of cells to generate a control-cell DNA and a test-cell DNA;

b) cleaving the control-cell DNA and the test-cell DNA with a master restriction enzyme to generate cleaved control-cell DNA and cleaved test-cell DNA;

c) preparing a probe from a DNA isolated by the methods of the present invention, for example, a DNA selected from the group consisting of SEQ ID NO:7–10;

d) hybridizing the probe to the cleaved control-cell DNA and the cleaved test-cell DNA to form a control-hybridization complex and a test-hybridization complex; and e) observing whether the size of the control-hybridization complex is the same as the size of the test-hybridization complex.

Similarly, the present invention provides a method of detecting whether a DNA site is mutated in a genomic DNA present in a test sample of cells which includes:

a) isolating genomic DNA from a control sample of cells and a test sample of cells to generate a control-cell DNA and a test-cell DNA;

b) cleaving the control-cell DNA and the test-cell DNA with a detector restriction enzyme to generate cleaved control-cell DNA and cleaved test-cell DNA;

c) preparing a probe from a discrete DNA isolated by the methods of the present invention;

d) hybridizing the probe to the cleaved control-cell DNA and the cleaved test-cell DNA to form a control-hybridization complex and a test-hybridization complex; and e) observing whether the size of the control-hybridization complexes the same as the size of the test-hybridization complex;

wherein the detector restriction enzyme does not cleave a mutated DNA site but does cleave a corresponding nonmutated DNA site.

Hybridization techniques for detecting specific genomic DNA fragments are known in the art and include solid-phase-based hybridization and solution hybridization which use any of the known reporter molecules. Detailed methodology for gel electrophoretic and nucleic acid hybridization techniques can be found in Sambrook et al.

Preferred nucleic acid probes for detecting hypomethylation and hypermethylation have SEQ ID NOS:7–10.

According to the present invention, a probe isolated by the subject methods, can be labeled by any procedure known in the art, for example by incorporation of nucleotides linked to a "reporter molecule".

A "reporter molecule", as used herein, is a molecule which provides an analytically identifiable signal allowing detection of a hybridized probe. Detection may be either qualitative or quantitative. Commonly used reporter molecules include fluorophores, enzymes, biotin, chemiluminescentmolecules, bioluminescent molecules, digoxigenin, avidin, streptavidin or radioisotopes. Commonly used enzymes include horseradish peroxidase, alkaline phosphatase, glucose oxidase and $\beta$-galactosidase, among others. Enzymes can be conjugated to avidin or streptavidin for use with a biotinylated probe. Similarly, probes can be conjugated to avidin or streptavidin for use with a biotinylated enzyme. The substrates to be used with these enzymes are generally chosen for the production, upon hydrolysis by the corresponding enzyme, of a detectable color change. For example, p-nitrophenyl phosphate is suitable for use with alkaline phosphatase reporter molecules; for horseradish peroxidase, 1,2-phenylenediamine, 5-aminosalicylic acid or tolidine are commonly used.

Incorporation of a reporter molecule into a DNA probe can be by any method known to the skilled artisan, for example by nick translation, primer extension, random oligo priming, by 3' or 5' end labeling or by other means (see, for example, Sambrook et al.).

In another embodiment, the present invention provides one or more compartmentalized kits for detection of hypomethylation. A first kit has a receptacle containing at least one of the present isolated probes. Such a probe may be a nucleic acid fragment which is methylated at a CNG trinucleotide in the genomic DNA of normal cells but which is not methylated in the genomic DNA of cancerous cells. Such a probe may be specific for a DNA site that is normally methylated but which is nonmethylated in certain cell types. Similarly, such a probe may be specific for a DNA site that is abnormally methylated or hypermethylated in certain cell types. Finally, such a probe may identify a specific DNA mutation. By specific for a DNA site is meant that the probe is capable of hybridizing to the DNA sequence which is mutated or abnormally methylated, or is capable of hybridizing to DNA sequences adjacent to said mutated or abnormally methylated DNA sequences. The probe provided in the present kits may have a covalently attached reporter molecule.

A second kit has at least one receptacle containing a reagent for MDD. Such a reagent can be, for example, a preferred master restriction enzyme, a preferred partner restriction enzyme, a preferred adaptor which can be ligated to DNA cut with the preferred master restriction enzyme, a primer that hybridizes to a preferred adaptor, and the like.

Using the MDD methods of the present invention, several methyl-polymorphic markers or sites in the human genome have been identified and DNA fragments encoding these marker sites have been isolated from different cell types. In particular, the present MDD methods have been used to identify hypomethylated sites which act as markers indicating whether a patient has cancer. These sites were identified using B-cells from patients with Chronic Lymphocytic Leukemia (CLL) and using tumor cells from breast cancer patients.

Moreover, for the first time the present methods and probes experimentally prove that methylated external cytosine at CpCpG triplet sequences do exist in the human genome, and that alteration of their methylation patterns is related to human cancer development. According to the present invention, methylation of the first base of CpCpG triplets is not a random event. Instead, it is a site- and tissue-specific event.

The alteration of the methylation pattern in CpCpG triplets may be a key, and common event, in the development of neoplasia. Imbalanced methylation at CpCpG triplet may play at least two roles in tumorigenesis:

1) DNA hypomethylation may cause some proto-oncogene expression or DNA hypermethylation may silence a tumor supressor which contributes to neoplastic growth; and 2) DNA hypomethylation may change chromatin structure, and induce abnormalities in chromosome pairing and disjunction. Such structural abnormalities may result in genomic lesions, such as chromosome deletions, amplifications, inversions, mutations, and translocations, all of which are found in human genetic diseases and cancer.

Hence, the present MDD methods have broad utility for identifying differentially methylated sites at CpCpG triplet sequences in the human genome; for mapping hypo- and hyper-methylation sites which are related to disease development; for understanding the role(s) of DNA methylation in normal cell genomic DNA imprinting, differentiation, and development; for understanding tumorigenesis; for diagnosing and monitoring the prognosis of disease; and for searching for proto-oncogene(s) and recessive oncogene(s). MDD, as a comprehensive molecular genetic technique, enables the accumulation of knowledge necessary to help better understand the etiology of human genetic diseases and cancer.

The methods of the present invention permit identification and isolation of genomic nucleic acids which are differentially methylated or differentially expressed among tissues of different types. Using the nucleotide sequences provided, oligonucleotides can be constructed which are useful as reagents for detecting the susceptibility of particular DNA sequences in a test sample to cleavage by restriction endonucleases. Such susceptibility to cleavage is affected by factors which include methylation of particular bases and the substitution of bases through mutation. For example, from the sequences provided, it is possible to generate nucleic acid probes to determine the sizes and relative amounts of particular DNA species which result when DNA recovered from a test sample is digested with selected sequence specific endonucleases.

The genomic nucleic acids isolated by the present invention, or oligonucleotides obtained therefrom, can also be used to detect and isolate expression products, for example, mRNA, complementary DNAs (cDNAs) and proteins derived from or homologous to the present genomic nucleic acids. In one embodiment, the expression of mRNAs homologous to the nucleic acids of the present invention is detected, for example, by Northern analysis, reverse transcription or amplification by PCR. Such procedures permit detection of mRNAs in a variety of tissue types or at different stages of development. The subject nucleic acids which are expressed in a tissue-specific or a developmental-stage-specific manner are useful as tissue-specific markers or for defining the developmental stage of a sample of cells or tissues. One of skill in the art can readily adapt the present nucleic acids and oligonucleotides for these purposes. Useful hybridization conditions for probes and primers made according to the present invention are readily determinable by those of skill in the art. Preferred stringent hybridization conditions are those which allow hybridization of nucleic acids which are greater than 90% homologous but which prevent hybridization of nucleic acids which are less than 70% homologous.

In another embodiment of the present invention, cDNAs homologous to the present nucleic acids can be isolated by procedures readily available to those of skill in the art. For example, cDNA libraries can be obtained from the tissues or cells which express the present genomic nucleic acids. Those cDNA libraries can then be probed with a genomic nucleic acid isolated by the methods of the present invention, or an oligonucleotide fragment thereof. Again, one of skill in the art can readily isolate such cDNAs using the genomic nucleic acids of the present invention.

The present genomic and cDNA nucleic acids can be used to prepare oligonucleotides. In one embodiment, oligonucleotides having twelve nucleotides or more can be prepared which hybridize specifically to the present genomic nucleic acids and cDNAs and allow detection and isolation of unique nucleic sequences by hybridization. Sequences of at least 15–20 nucleotides are preferred and are selected from regions which lack homology to other known sequences. Sequences of 20 or more nucleotides which lack such homology are optimal.

Genomic nucleic acids isolated by the present procedures include BR50 (SEQ ID NO:10), BR104 (SEQ ID NO:7) and BR254 (SEQ ID NO:8), clones which are hypomethylated in breast cancer cells. A cDNA clone identified as TSP50 (SEQ ID NO:14) was obtained by virtue of its homology to the BR50 (SEQ ID NO:10) genomic clone. Each of these nucleic acids is useful for detecting hypomethylation and expression of homologous nucleic acids in a variety of normal and cancerous cells or tissues. Each of these nucleic acids is also useful for identifying homologous genomic and cDNA nucleic acids.

Oligonucleotides useful as probes for screening of samples by hybridization assays or as primers for amplification can be packaged into kits. Such kits usually contain the probes or primers in a premeasured or predetermined amount, as well as other suitably packaged reagents and materials needed for the particular hybridization or amplification protocol.

In another embodiment, the present genomic and cDNA nucleic acids can be placed in expression vectors capable of expressing an encoded protein, polypeptide or peptide. Nucleic acids encoding a desired protein or polypeptide are derived from cDNA or genomic clones using conventional restriction digestion or by synthetic methods, and are ligated into vectors from which they may be expressed. Vectors may, if desired, contain nucleic acids encoding portions of other proteins, thereby providing a fusion protein. For example, portions of the β-galactosidase or superoxide dismutase coding region may be placed in frame with the present coding regions to provide an expression vector which encodes a fusion protein.

Expression vectors include plasmids designed for the expression of proteins or polypeptides fused to or within bacterial phage coat proteins. The DNA encoding the desired protein or polypeptide, whether in a fusion, premature or mature form, may be ligated into expression vectors suitable for any host. The DNA encoding the desired polypeptide may also contain a signal sequence to permit secretion from the intended host. Both prokaryotic and eukaryotic host systems are contemplated.

The present proteins, polypeptides and peptides, whether in a premature, mature or fused form, are isolated from lysed cells, or from the culture medium, and are purified to the extent needed for the intended use. One of skill in the art can readily purify these proteins, polypeptides and peptides by any available procedure. For example, purification may be accomplished by salt fractionation, size exclusion chromatography, ion exchange chromatography, reverse phase chromatography, affinity chromatography and the like.

The present invention further contemplates antibodies which can bind to the present proteins, polypeptides and peptides. Such antibodies preferably bind to unique antigenic regions or epitopes in the present proteins, polypeptides and peptides. Unique antigenic regions or epitopes of a protein are generally small, often eight to ten amino acids or less in length. An epitope or antigenic region may be defined by a sequence of as few as 5 amino acids.

Epitopes and antigenic regions useful for generating antibodies can be found within the present proteins, polypeptides or peptides by procedures available to one of skill in the art. For example, short, unique peptide sequences can be identified in the present proteins and polypeptides that have little or no homology to known amino acid sequences. Preferably the region of a protein selected to act as a peptide epitope or antigen is not entirely hydrophobic; hydrophilic regions are preferred because those regions likely constitute surface epitopes rather than internal regions of the present proteins and polypeptides. These surface epitopes are more readily detected in samples tested for the presence of the present proteins and polypeptides.

Peptides can be made by any procedure known to one of skill in the art, for example, by using in vitro translation or chemical synthesis procedures.

Short peptides which provide an antigenic epitope but which by themselves are too small to induce an immune response may be conjugated to a suitable carrier. Suitable carriers and methods of linkage are well known in the art. Suitable carriers are typically large macromolecules such as proteins, polysaccharides and polymeric amino acids. Examples include serum albumins, keyhole limpet hemocyanin, ovalbumin, polylysine and the like. One of skill in the art can use available procedures and coupling reagents to link the desired peptide epitope to such a carrier. For example, coupling reagents can be used to form disulfide linkages or thioether linkages from the carrier to the peptide of interest. If the peptide lacks a disulfide group, one may be provided by the addition of a cysteine residue. Alternatively, coupling may be accomplished by activation of carboxyl groups.

The minimum size of peptides useful for obtaining antigen specific antibodies can vary widely. The minimum size must be sufficient to provide an antigenic epitope which is specific to the protein or polypeptide. The maximum size is not critical unless it is desired to obtain antibodies to one particular epitope. For example, a large polypeptide may comprise multiple epitopes, one epitope being particularly useful and a second epitope being immunodominant. Typically, antigenic peptides selected from the present proteins and polypeptides will range from 5 to about 100 amino acids in length. More typically, however, such an antigenic peptide will be a maximum of about 50 amino acids in length, and preferably a maximum of about 30 amino acids. It is usually desirable to select a sequence of about 10, 12 or 15 amino acids, up to a maximum of about 20 or 25 amino acids.

Amino acid sequences comprising useful epitopes can be identified in a number of ways. For example, the entire protein sequence can be screened by preparing a series of peptides that together span the entire protein sequence. One of skill in the art can routinely test a few large polypeptides for the presence of an epitope showing a desired reactivity and also test progressively smaller and overlapping fragments to identify a preferred epitope with the desired specificity and reactivity.

Antigenic polypeptides and peptides are useful for the production of monoclonal and polyclonal antibodies. To obtain polyclonal antibodies, a selected animal is immunized with a protein or polypeptide. Serum from the animal is collected and treated according to known procedures. Polyclonal antibodies to the protein or polypeptide of interest may then be purified by affinity chromatography. Techniques for producing polyclonal antisera are will known in the art.

Monoclonal antibodies may be made by procedures available to one of skill in the art, for example, by fusing antibody producing cells with immortalized cells and thereby making a hybridoma. The general methodology for fusion of antibody producing B cells to an immortal cell line is well within the province of one skilled in the art.

The present antibodies are useful for detecting the present proteins and polypeptides in specific tissues or in body fluids. Moreover, according to the present invention, detection of aberrantly expressed proteins or protein fragments is probative of a disease state. For example, expression of the present proteins or polypeptides from a hypomethylated genomic locus may indicate that the protein is being expressed in an inappropriate tissue or at an inappropriate developmental stage. Hence, the present antibodies are useful for detecting diseases associated with protein expression from improperly methylated genomic loci, for example, the types of cancers and genetic diseases contemplated herein.

Design of immunoassays is subject to a great deal of variation and a variety of these are known in the art. Immunoassays may use a monoclonal or polyclonal antibody reagent which is directed against one epitope of the antigen being assayed. Alternatively, a combination of monoclonal or polyclonal antibodies may be used which are directed against more than one epitope. Protocols may be based, for example, upon competition, direct antigen-antibody reaction or sandwich type assays. Protocols may, for example, use solid supports or immunoprecipitation. The present antibodies can be labeled with a reporter molecule for easy detection. Assays which amplify the signal from a bound reagent are also known. Examples include immunoassays which utilize avidin and biotin, or which utilize enzyme-labeled antibody or antigen conjugates, such as ELISA assays.

Kits suitable for immunodiagnosis and containing the appropriate labeled reagents include antibodies directed against the present protein epitopes or antigenic regions, packaged appropriately with the remaining reagents and materials required for the conduct of the assay, as well as a suitable set of assay instructions.

The following examples further illustrate the invention.

EXAMPLE 1

Materials and Methods

To test the MDD technique, a working model system was designed to isolate methyl-polymorphic DNA markers (see FIG. 1 for a schematic diagram of the MDD methods). There is evidence that in mammalian DNA, methylation patterns are both tissue-, and cell-type specific. Hence, DNA was isolated from two different types of cells from patients who have chronic lymphocytic leukemia (CLL). In CLL patients, the number of $CD5^+$ B type lymphocytes is abnormally high. These $CD5^+$ cells can be isolated by highly specific antibodies in a fluorescence activated cell sorter (FACs). For performing MDD, the DNA isolated from these $CD5^+$ cells served as the tester, while DNA isolated from neutrophils of the same patient served as the driver. A methyl-polymorphic DNA probe, named CLL58, which exhibited methyl-differential displays was isolated from an individual CLL patient.

After the successful isolation of these methyl-polymorphic probes, MDD was again successfully used in the isolation of methyl-polymorphic probes from breast cancer biopsies. Three methyl-polymorphic probes, BR50, BR104, and BR254, which gave methyl-differential displays in breast cancer and their matched normal cells, were isolated from three individual patients. BR50 and BR254 also gave methyl-differential displays in ovarian cancer and their matched normal cells, while the BR254 probe exhibited a methyl-differential display in colon cancer cells.

DNA Isolation from Malignant B-cells and Neutrophil Cells

Mononuclear and neutrophil cells were isolated from the peripheral whole blood of CLL patients by Ficoll/Hypage centrifugation. Leukemic B-cells ($CD5^+$), were sorted from mononuclear cells in the presence of fluorescent anti-CD5 antibodies by FACs. DNAs were isolated by the phenol extraction method. Sambrook, J., Fritsch, E. F. and Maniatis, T., (1989) Molecular Cloning, 9.16–9.19.

DNA from Human Cancer Biopsies

Dissected human breast, ovarian, and colon cancer tissues (tumor and normal) were immediately frozen in liquid nitrogen, and stored at −70° C. DNAs were isolated from both tumor and matched normal tissues by the phenol extraction method. Sambrook, J., Fritsch, E. F. and Manitis, T., (1989) Molecular Cloning, 9.16–9.19.

MDD

To prepare tester and driver amplicons, 1–2 μg of tester and driver genomic DNA were digested simultaneously with Msp I and Mse I restriction endonucleases (New England Biolabs). The digested DNAs were extracted with phenol/chloroform once, and precipitated with 2 volumes of ethanol after adding 1/10 volume of 3 M NaAc.

The DNAs were then resuspended in 10 μl of TE buffer (10 mM Tris-HCl, 0.1 mM EDTA, pH8.0). To ligate the first pair of oligonucleotide adapters (MSA24 with SEQ ID NO:1 and MSA12 with SEQ ID NO:2) to the digested tester and driver amplicon DNAs, 10 μl (1 μg) of digested DNA was mixed with: 2.5 μl of each of the unphosphorylated single strand adapters having SEQ ID NO:1 (0.6 μg/μl) and SEQ ID NO:2 (0.3 μg/μl); 2 μl of 10×ligation buffer (Boehringer Mannheim); and 3 μl of $ddH_2O$. The oligonucleotide adapters were annealed by cooling the mix gradually from 55° C. to 10° C. over a 1.5 hour period in a 4° C. cold room, and then ligated to Msp I/Mse I-cut DNA fragments by overnight incubation with 1 U of T4 DNA ligase (Boehringer Mannheim) at 16° C. After ligation, the ligate was diluted with TEt buffer (10 mM Tris-HCl, 0.1 mM EDTA, 20 μg/ml of tRNA) at a concentration of 2 ng/μl.

To generate the tester and driver amplicons, tester and driver DNA ligated to the first set adapters were separately amplified by polymerase chain reaction ("PCR"). Two PCR tubes were set up to make the tester amplicon, while five PCR tubes were prepared for the driver amplicon. Each tube has a 400 μl reaction mixture containing 67 mM Tris-HCl, pH 8.8 at 25° C., 4 mM $MgCl_2$, 16 mM $(NH_4)_2SO_4$, 10 mM β-mercaptoethanol, 100 μg/ml of non-acetylated bovine serum albumin, 24 μl of dNTP (5 mM for each dATP, dCTP, dGTP, and dTTP), 8 μl of SEQ ID NO:1 (0.6 μg/μl), and 80 ng of DNA ligated to the adapters as templates. While the tubes were equilibrated at 72° C. in a thermal cycler (Perkin-Elmer Cetus), 12 U of Taq DNA polymerase (Perkin-Elmer Cetus), and 3 U of pwo DNA polymerase (Boehringer Mannheim) were added. The reaction was overlaid with mineral oil and incubated for 5 minutes to fill-in the 3'-recessed ends of the ligates, and the DNAs were then amplified by 24 cycles of PCR. Each PCR cycle included 1 minute at 95° C., 1 minute at 67° C. and 3 minutes at 72° C., and the last cycle was followed with a 10 minute extension time at 72° C. The DNA amplicons were extracted once with phenol, once with phenol/chloroform, and precipitated by 2 volumes of 100% ethanol after adding 1/4 volume of 10 M $NH_4Ac$. Amplicon DNAs were then resuspended in TE buffer.

To remove the first set of adapters from the driver amplicon, 80 μg of driver amplicon DNA was digested to completion with Msp I enzyme (10U/μg). The driver amplicon DNA was extracted once with phenol/chloroform, and after adding 1/4 volume of 10 M $NH_4Ac$, the DNA was precipitated with 2 volumes of 100% ethanol. The amplicon DNA was resuspended in TE buffer at a concentration of 0.5 μg/μl. To change the tester amplicon DNA adapters, 5 μg of tester amplicon was digested with Msp I (10 U/μg). The digested tester amplicon DNA was purified by PCR purification spin column (Boebringer Mannheim).

For the hybridization/subtraction and amplification steps, Msp I digested tester amplicon DNA was ligated to a second set of adapters (MSB24 having SEQ ID NO:3 and MSB12 having SEQ ID NO:4): 1 μl (0.2 μg) of digested tester DNA was mixed with 1 μl of the SEQ ID NO:3 adaptor (0.6 μg/μl), 1 μl of the SEQ ID NO:4 adaptor (0.3 μg/μl), 1 μl of 10×ligation buffer, and 6 μl of $ddH_2O$. The same annealing and ligation steps were performed as for ligation of the first set of adapters. After ligation, the ligate was diluted with 40 μl of TEt buffer and mixed with 20 μg (40 μl) of driver amplicon DNA. The mix was extracted with phenol/chloroform once, and precipitated by adding 1/4 volume of 10 M $NH_4Ac$, and 2.5 volumes of 100% ethanol in a dry ice/ethanol bath for 10 minutes. The reaction solution was equilibrated to room temperature and the DNA was collectedly centrifugation. The pellet was washed twice with 70% ice cold ethanol, dried, resuspended in 2 μl of 3×EE buffer.

D. Straus et al., 87 Proc. Natl. Acad. Sci. USA 1889 (1990). After resuspension, the DNA was overlaid with one drop of mineral oil (Perkin-Elmer Cetus), denatured at 100° C. for 5 minutes, and 0.5 μl of 5 M NaCl was added. The DNAs were hybridized at 68° C. for at least 20 hours.

To amplify the difference products (DP1), the 3'-recessed ends were first filled in with DNA polymerase. The hybridized product was diluted with 198 μl of TE buffer, and a 50 μl of filling-in reaction was set up: 30 μl of diluted DNA hybrids, 10 μl of 5×PCR buffer, 2 μl of dNTP (5 mM for each dATP, dCTP, dGTP, and dTTP), and 8 μl of ddH$_2$O. The reaction was equilibrated at 72° C., 3 U of Taq DNA polymerase (Perkin-Elmer Cetus) and 0.75 U of pwo DNA polymerase (Boehringer Mannheim) were added at 72° C. for 10 minutes. The filled-in DNA hybrids were purified by a PCR purification spin column (Boehringer Mannheim).

To reduce the background for DP1 amplification, mung bean nuclease treatment of the filled-in DNA hybrids was performed: 9 μl of filled-in DNA hybrid solution mixed with 1 μl of 10×mung bean nuclease reaction buffer and 50 U of mung bean nuclease (Boehringer Mannheim) was incubated at 30° C. for 30 minutes. The reaction was terminated by heat inactivation at 100° C. for 5 minutes after adding 40 μl of 50 mM Tris-HCl (pH 8.9).

To amplify DP1, 1 tube of 100 μl PCR reaction was set up. The reaction consisted of: 20 μl of mung bean nuclease-treated DNA hybrid solution, 20 μl of 5×PCR buffer, 5 μl of dNTP (5 mM for each dATP, dCTP, dGTP. and dTTP), 2 μl of the SEQ ID NO:3 adaptor, and 52 μl of ddH$_2$O. The reaction was hot started at 94° C. for 2 minutes after adding 3 U of Taq DNA polymerase (Perkin-Elmer Cetus) and 0.75 U of pwo DNA polymerase (Boehringer Mannheim). The conditions for the PCR were 1 minute at 95° C., 1 minute at 67° C., and 3 minutes at 72° C. for 35–40 cycles. The last cycle was followed with a 10 minutes extension step at 72° C. The DP1 was purified by PCR purification spin column (Boehringer Mannheim), and the concentration of the DNA was determined at OD$_{260}$ in a spectrophotometer.

To prepare the second round of hybridization/subtraction and amplification steps, 3 μg of DP1 was digested with the restriction endonuclease Msp I (10 U/μg) in a 30 μl reaction. The digested DP1 was purified with PCR purification spin column (Beohringer Mannheim).

To put a new set of adapters (MSC24 having SEQ ID NO:5 and MSC12 having SEQ ID NO:6) on DP1, 2 μl (0.1 μg) of DP1 was mixed with 1 μl of the MSC24 adaptor (0.6 μg/μl), 1 μl of the MSC12 adaptor (0.3 μg/μl), 1 μl of 10×ligation buffer (Beohringer Mannheim), and 6 μl of ddH$_2$O. The annealing and ligation reactions were done as before. The ligate was diluted with 40 μl of TEt buffer to the concentration of 2 ng/μl.

To set up the hybridization reaction, 20 ng (10 μl) of diluted ligate was mixed with 20 μg (40 μl) of driver amplicon DNA. The DNA mix was extracted with an equal volume of phenol/chloroform once, and precipitated with 2.5 volumes of 100% ethanol after adding 1/4 volume of 10 M of NH$_4$Ac in a dry ice/ethanol bath for 10 minutes. The reaction solution was equilibrated to room temperature and the DNA was collected by centrifugation. The pellet was washed twice with 70% ice cold ethanol, dried, and resuspended in 2 μl of 3×EE. 0.5 μl of 5 M Nace was added after the DNA mix was denatured at 100° C. for 5 minutes. The hybridization reaction was carried out at 68° C. for a minimum period of 20 hours.

To amplify the secondary different product (DP), the hybrids were diluted with 198 μl of TE buffer, and 100 μl of PCR amplification reaction was set up as follows: 4 μl of the diluted hybrid solution, 5 μl of dNTP (5 mM for each dATP, dCTP, dGTP, dTTP), 20 μl of 5×PCR reaction buffer, and 69 μl of ddH$_2$O. While the PCR tube was equilibrated at 72° C., 3 U of Taq DNA polymerase (Perkin-Elmer Cetus) and 0.75 U of pwo DNA polymerase (Boehringer Mannheim) were added to fill-in the 3'-recessed ends for 10 minutes. 2 μl of the MSC24 adaptor (0.6 μg/μl) was then added. The PCR reaction was hot started by raising the temperature to 94° C. for 2 minutes, and 35 to 40 cycles of PCR reaction were performed under the same conditions as were used for amplifying DP1.

DP usually contained several individual DNA fragments when electrophoresed on a 2% agarose gel. The individual DNA fragments were purified by DNA gel extraction kit (Qiagen Inc.), and subcloned into pUC118 vector, which was linearized by the restriction endonuclease Acc I. If the DP product had some DNA smear, it was treated with mung bean nuclease as described above.

For each MDD, twelve to twenty colonies were chosen to amplify their inserts, from which different sized probes were selected for amplicon Southern blotting, and human genomic DNA Southern blotting.

Amplicon DNA Southern Blot

The first round of positive probe screening was performed with amplicon DNA Southern blots. Non-Radiation Southern blot and Detection Kits (Genius™) were purchased from Boehringer Mannheim. Probe labeling, and detection followed the instruction of the manufacturer.

Two to three μg of tester and driver amplicon DNA were electrophoresed on a 2% agarose gel, and blotted to positively charged nylon membranes (Boehringer Mannheim). For prehybridization, the membranes were placed at 68° C. for 2–4 hours in solutions containing 6×SSC, 5×Denhardt's solution, 0.5% SDS, 0.1 M EDTA, and 50 μg/ml of salmon sperm DNA. Under the same conditions, the probes were added, and hybridized to the membranes overnight. The membranes were then rinsed three times with 2×SSC, 1×blot wash (12 mM Na$_2$HPO$_4$, 8 mM NaH$_2$PO$_4$, 1.4 mM Na$_4$P$_2$O$_7$, 0.5% SDS) at 68° C., and further washed three times (30 minutes for each time) with the same buffer at 68° C. Next, the membranes were equilibrated in buffer A (100 mM Tris-HCl, 150 mM, pH 7.5) and transferred into buffer B (2% black reagent in buffer A) solution and incubated at room temperature for one hour. The membranes were then washed 2 times (15 minutes for each time) with buffer A, and equilibrated in buffer C (100 mM Tris-HCl, 100 mM NaCl, 10 MM MgCl$_2$). Before the membranes were exposed on Kodak X-OMAT film, they were rinsed in lumi-P530 for 1 min and kept in a plastic sheet protector. Positive clones were identified by observing the probe hybridized more heavily to test amplicon DNA than to driver amplicon DNA.

Human Genomic DNA Southern Blot

The positive probes that were confirmed by the amplicon DNA Southern blot experiment were tested further by human genomic DNA Southern blotting. Genomic DNAs isolated from cancer tissues, and their respective matched normal tissues, were digested with Msp I restriction endonuclease, electrophoresed on 1.5% agarose gels, and transferred to Hybond Membranes (Amersham, Arlington Heights, Ill.) These membranes were exposed to UV light to immobilize the DNA. The probes for the Southern blot were labeled with High Prime DNA labeling kits (Boehringer Mannheim) following the instructions of the manufacturer. The procedure for hybridization and blot wash were the same as in the Amplicon DNA Southern blotting section.

EXAMPLE 2

Different Methylation Patterns at CpCpG Sites in Malignant B-cells and Neutrophil Cells DNA isolated from malignant B-cells and neutrophil cells of four CLL patients (#58, #111, #112, #128) was used to perform MDD as described above in the Materials and Methods provided in Example 1. The DNA from leukemic B-cells was used as the tester, and the DNA from neutrophil cells was used as the driver. Tester and driver DNAs were simultaneously digested with the restriction endonucleases, Msp I and Mse I. After ligating the first set of adapters to the digested tester and driver DNA fragments, tester and driver amplicons were generated by PCR amplification (see Materials and Methods). After two rounds of hybridization/ subtraction and amplification, the difference products (DP) which were isolated from patient 111 appeared as individual DNA fragment bands on an agarose gel (FIG. 2). The DP fragments were then subcloned into the plasmid pUC118 (see Materials and Methods), and amplified by PCR. For the first round of selection, inserts of different sizes were selected and hybridized to the tester and driver amplicon DNAs from which they were derived in a non-radioactive Southern blot experiment (see materials and methods). The positive probes were selected if they hybridized a single band in the tester amplicon only, or if they hybridized to both tester and driver amplicon DNA, but the hybridization to the driver amplicon DNA band was far less intense. The final proof of a positive probe was that it displayed a different methylation pattern in a genomic DNA Southern blot experiment in which the parental malignant B-cell, and normal neutrophil cell genomic DNA, were digested with the restriction endonuclease Msp I (see materials and methods).

The CLL58 probe isolated from patient #111 fulfilled these requirements. When CLL58 was hybridized to its tester and driver amplicon DNA, the tester amplicon DNA gave a heavy hybridization band, while the driver amplicon DNA gave a much less intense hybridized band (FIG.3).

The CLL58 probe was further tested by hybridization to a genomic Southern blot of Msp I-digested malignant B-cell and neutrophil cell DNA. The genomic Southern blot revealed that a larger fragment was much less intensely hybridized than a lower molecular weight fragment in the malignant B-cell DNA, while in the neutrophil cell DNA, just the opposite result occurred (FIG. 4). These results demonstrate that in human genomic DNA, there are methylated external cytosine residues at CpCpG sequences, and those CpCpG sequences are differentially methylated in different types of cells. Moreover, the CLL58 probe can detect and distinguish cell-type specific methylation patterns.

EXAMPLE 3

MDD-Isolated Probes from Human Breast Cancer Tumors also Detect Ovarian and Colon Cancers We have proven the existence of methylation of the external cytosine residue at CpCpG sites in the human genome, and have isolated CpCpG site related methyl-polymorphic markers in a working model system. MDD was then applied to successfully isolate CpCpG related methyl-polymorphic markers from human breast cancer biopsies.
Isolation of Probes From Breast Tumor DNA MDD was used to test five pairs of DNA samples (tumor DNA and matched normal DNA) obtained from five breast cancer patients. To isolate methyl-polymorphic markers, tumor DNA served as the tester, and normal DNA served as the driver. MDD was performed in the same manner as described in Example 1. Individual DNA fragments were isolated by MDD from three breast cancer patients after two rounds of hybridization/subtraction and amplification (FIG. 5).

Three probes were further analyzed, BR50, BR104, and BR254, isolated from patient #14, patient #13, and patient #4, respectively. Each of these three probes appropriately hybridized with their own tester amplicon DNA, but also hybridized slightly with the driver amplicon DNA (FIGS. 6a–c).

These probes were then examined further by hybridizing them to Msp I-digested parental tumor and matched normal genomic DNAs. The genomic Southern blot for probe BR50 showed that the probe hybridized with a lower band to a much greater degree than to an upper band in tumor DNA (FIG. 7a). However, in normal DNA, just the opposite occurred—the BR50 probe hybridized to the upper band more than to the lower band (FIG. 7a).

The genomic DNA Southern blot for probe BR104 showed that the probe hybridized with a lower and a middle band in the tumor DNA, while in the normal DNA, probe BR104 hybridized with a middle and an upper band (FIG. 7b).

For the probe BR254, the Southern blot result showed that it hybridized with a lower band and a upper band in the tumor DNA, however, it only hybridized with an upper band in the normal DNA (FIG. 7c).

The results of three cases, indicate that in normal cells the genomic DNA is more highly methylated, is cut less frequently and gives rise to larger fragments than is observed for DNA from tumor cells. The isolated probes therefore hybridize to higher molecular weight bands in normal DNA. In contrast, the lower bands which were hybridized with probes BR50, BR104, and BR254, are generated by demethylation of the external C residue at CpCpG DNA sites in the tumor cells. The weakly hybridized upper bands in the tumor DNA are likely caused by normal cell contamination.
Breast Tumor Probes Detect Hypomethylation in Other Cancer Patients To understand whether this hypomethylation event also happens in other breast cancer patients, normal cell and tumor cell DNA was isolated from ten breast cancer patients, cleaved by the Msp I enzyme, and probed with BR50 and BR104. Of the ten breast patients whose DNA was probed with BR50, five had a hybridization pattern which was similar to that of the patient from which BR50 was isolated (the "parental patient") (FIG. 8). Of the ten breast patients whose DNA was probed with BR104, five had a hybridization pattern similar to that of the parental patient. (See FIG. 9, providing four of these five patterns).

The BR254 probe was hybridized to normal and tumor DNA of 16 breast cancer patients. Of the 16 patients, 10 had a hybridization pattern which was similar to that of the parental patient. However, some differences in the methylation patterns of these patients were observed. Some patients only had the lower band in their tumor DNA, and the upper band in their normal DNA (FIG. 10). However, other patients had the lower band in their tumor DNA, but had both lower and upper bands in their normal DNA (FIG. 10). These results indicate that the external cytosine residue at CpCpG sites are fully demethylated in some breast tumors. However, the lower bands appearing in normal DNAs probably were caused by a partial demethylation event, which suggests that the normal cells were under the process of neoplastic change. In general, the different extent of demethylation identified by probes BR50, BR104, and BR254 in human breast cancer patients is a common phenomena and may be used to predict the extent of neoplastic change.
Detection of a DNA Amplification Event in a Breast Cancer Patient The BR254 probe detected a highly amplified DNA event in one of the 16 breast cancer patients tested with that probe (FIG. 11). This result provides evidence that imbalanced DNA methylation may cause a conformational change of chromatin which then induces a DNA amplification.

Hypomethylation Detection by BR50, BR104, and BR254 in Ovarian Cancers.

To examine whether the same hypomethylation phenomena also happens in human ovarian cancer, DNA samples isolated from 8 patients with ovarian cancer were analyzed. For some patients, two DNA samples were obtained, one from primary ovarian cancer tissue, and the other from their matched normal tissue. For other patients, three DNA samples were obtained, they were from primary ovarian cancer tissue, metastatic tumor tissue, and matched normal tissue. The DNAs were cleaved with Msp I, and hybridized with the probes BR50 and BR104 in Southern blot experiments.

Of the eight ovarian patients tested with the BR50 probe, five patients had similar hybridization patterns: the BR50 probe hybridized almost equally to lower and upper bands in their normal DNA samples, while in the primary tumor DNA, the upper band was only slightly hybridized. However, in the metastatic tumor DNA of these 5 patients, only the lower band was hybridized (FIG. 12).

No different hybridization patterns were detected using the probe BR104. This result indicates that the BR104 probe was detecting a tissue-specific hypomethylation event.

Eleven patients' DNA samples were examined using the BR254 probe. The Southern blot results showed that of 11 patients, 4 had the same hybridization patterns which appeared in the parental DNA pair (FIG. 13).

These results suggest that probes BR50 and BR254 detect tumor-related hypomethylation events in both breast and ovarian cancer cells. Interestingly, in the case of probe BR50, the complete disappearance of the upper band in the metastatic tumor DNA indicates that the extent of demethylation seems to be related to the progression of the disease.

Hypomethylation Detection using BR50, BR104, and BR254 on Colon Cancer DNA

The methylation patterns of tumor and matched normal DNA samples isolated from 10 colon cancer patients were examined using BR50, BR104, and BR254 probes. DNAs were digested by the Msp I enzyme, Southern blots prepared and the blots were hybridized with these probes.

No difference in the methylation patterns of colon tumor DNA and normal DNA were detected by probes BR50 and BR104 (data not shown), indicating that both probes were detecting a tissue-specific hypomethylation event in colon cells.

However, for the probe BR254, different methylation patterns were observed. Of the ten colon cancer patients tested, six had hypomethylation patterns opposite to those observed for the breast and ovarian cancer patients. Instead of hybridizing more to an upper band in the normal DNA samples, probe BR254 hybridized with the lower band. Moreover, instead of hybridizing more to the lower band in the tumor DNA, BR254 hybridized equally with the lower band and a upper band (FIG. 14). These results demonstrate that while the BR254 probe detects hypomethylation in breast cancer cells, in colon cancer DNA the BR254 probe detects hypermethylation. Therefore, methylation patterns are not only tissue-type specific, but cancer-specific, and can be different in different types of cancers.

Sequencing and Chromosome Assignment of Probes BR50 and BR254

DNA sequencing showed that BR50 contains 1005 bp, with a CG content of 58% (SEQ ID NO:10); and BR254 contains 332 bp, with a CG content of 55% (SEQ ID NO:8).

Both probes have the nucleotide sequence GGCCGG at one end, and the nucleotide sequence CCGG sequence at the other end. Msp I, which cleaves at CCGG sequences, is sensitive to methylation at the external C residue, and will not cleave CmCGG. Thus, CCGG sequences at the ends of both probes were methylated in normal breast DNA and hypomethylated in tumor DNA.

Probes BR50 and BR254 were assigned to chromosome #3 and #8 respectively by genomic Southern blotting of the Hind III digested monochromosonal human/rodent somatic cell hybrid mapping panel #2 (NIGMS Human Genetic Mutant Cell Repository). showed that they are located on chromosome #3, and #8, respectively. Fine chromosome mapping was performed using GeneBridge 4 Radiation Hybrid Panel (Research Genetics, Inc.) as templates. Walter, M. A. et al., 7 NATURE GENETICS 22 (1994). BR50 is proximally located on 3p12–14, and BR254 is proximally located on 8q11–12. The adjacent Sequence Tagged Site (STS) to BR50 is AFMB362WB9, and to BR254 is WI-3862. A known oncogene, Fibroblast Growth Factor Receptor (FGFR) has been located on 8q11–12 region, and our results did show that the genomic region corresponding to BR254 was amplified in a breast cancer biopsy.

Determination of Coding Sequences $2 \times 10^6$ plaques from a human placenta genomic phage library, EMBL3 SP6/7 (ClonTech, Inc.) were screened with the probe BR50. A phage clone hybridizing to BR50 was obtained. The cloned genomic DNA was released by digestion with Sst I and transferred into pUC118. 8 DNA fragments were generated, and the total length of these fragments was approximately 17 kbp. Plasmids containing fragments smaller than 1 kbp were completely sequenced, while plasmids containing fragments larger than 1 kbp were partially sequenced. Homology searches against NIH GenBank revealed two exons, designated BR50-44 and BR50-45, consisting respectively of 112 and 132 nucleotides. Both regions displayed homology to several mammalian proteases, such as serine proteases and tryptases. Based on the sequence information obtained, oligomers were designed for the purpose of amplifying a cDNA sequence from a human universal cDNA library panel (ClonTech Inc.) A PCR product of about 682 bp was generated using one oligomer (SEQ ID NO:11) based on the sequence obtained from BR50-44 and a second oligomer (SEQ ID NO:12) based on the sequence obtained from BR50-45. This PCR product was directly sequenced. We obtained an incomplete coding sequence of 854 bp by combining the sequence obtained for the PCR product with sequences from BR50-44 and BR50-45. A DNA homology search against NIH GenBank again revealed similarity to serine proteases.

Tissue Specific Expression

Two commercially available tissue specific northern blot panels (Human Multiple Tissue Northern Blot, Human Multiple Tissue Northern Blot II, Clontech Inc.) containing poly A RNA from a total of 16 different human tissues were tested for the expression of an mRNA capable of hybridizing to the coding sequence described above. A probe (SEQ ID NO:13) corresponding to the portion of the coding sequence amplified by the oligomers of SEQ ID NO:11 and SEQ ID NO:12 hybridized strongly and specifically to a 1.3 kb testes specific transcript. Hybridization to the remaining 15 human tissues that were tested was not detected (FIG. 15). Therefore the locus was designated TSP50 (Testes Specific Protease).

Isolation of Full Length of cDNA

To obtain a full length TSP50 cDNA, a human testes cDNA A library (Clontech, Inc.) was screened with the TSP50probe having the nucleotide sequence given by SEQ ID NO:13. A cDNA clone consisting of 1,240 bp was obtained (SEQ ID NO:14). Sequence analysis indicates that this fragment encodes a protein containing 385 amino acids (SEQ ID NO:16). A stop codon located 117 bp upstream of the putative translation initiation site, and a 125 bp 3' untranslated region before a poly adenosine sequence suggest that a fill length coding sequence has been obtained.

What is claimed:

1. An isolated nucleic acid that specifically hybridizes to DNA that is hypomethylated in cancer cells, said isolated nucleic acid comprising a sequence having greater than 90% homology to SEQ ID NO:15, said nucleic acid encoding a complete human tsp50 protein.

2. The nucleic acid of claim 1 which comprises SEQ ID NO:15.

3. An isolated nucleic acid which encodes an amino acid sequence comprising SEQ ID NO:16 from about amino acid residue number 1 to about amino acid residue number 385.

4. A recombinant DNA comprising the isolated nucleic acid of any one of claims 1 to 3 operably linked to regulatory control sequences which effect expression of said nucleic acid in a host cell.

5. An expression vector comprising the recombinant DNA of claim 4.

6. A host cell comprising the expression vector of claim 5.

7. The host cell of claim 6 wherein said host cell is a eukaryotic or prokaryotic cell.

8. A process for producing a recombinant protein, which comprises:
   a) culturing the host cell of claim 6 in a culture medium under conditions suitable for expression of said protein in said host cell, and
   b) recovering said protein from said host cell or said culture medium.

9. An oligonucleotide that specifically hybridizes to DNA that is hypomethylated in cancer cells, said oligonucleotide comprising a sequence of at least about 12 adjacent nucleotides of SEQ ID NO:14 from nucleotide number 1 to nucleotide number 705 or the complement of SEQ ID NO:14 from nucleotide number 1 to nucleotide number 705.

10. An oligonucleotide that specifically hybrizes to DNA that is hypomethylated in cancer cells, said oligonuleotide comprising at least 15 adjacent nucleotides of SEQ ID NO:14 from nucleotide number 1 to nucleotide number 705 or the complement of SEQ ID NO:14 from nucleotide number 1 to nucleotide number 705.

11. The oligonucleotide of claim 10 having SEQ ID NO:11.

12. An oligonucleotide that specifically hybridizes to DNA that is hypomethylated in cancer cells, said oligonucleotide comprising at least 20 adjacent nucleotides of SEQ ID NO:14 from nucleotide number 1 to nucleotide number 705 or the complement of SEQ ID NO:14 from nucleotide number 1 to nucleotide 705.

13. An isolated nucleic acid that specifically hybrizes to DNA that is hypomethylated in cancer cells, said isolated nucleic acid comprising SEQ ID NO:13 from about nucleotide number 1 to about nucleotide number 682 or the complement of SEQ ID NO:13 from about nucleotide number 1 to about nucleotide number 682.

14. An isolated nucleic acid comprising SEQ ID NO:14 from about nucleotide number 1 to about nucleotide number 1240 or the complement of SEQ ID NO:14 from about nucleotide number 1 to about nucleotide number 1240.

15. A kit for identifying whether genomic DNA in a test sample is hypomethylated or hypermethylated in a region which comprises TSP50 DNA, said kit comprising a nucleic acid hybridization assay probe that specifically hybridizes to DNA that is hypomethylated in cancer cells, and probe comprising SEQ ID NO:15 or its complement, or a sequence having greater than 90% homology to SEQ ID NO:15 or its complement that encodes a complete human tsp50 protein and a restriction enzyme that cleaves nonmethylated DNA but does not cleave methlated DNA.

16. A kit for identifying TSP50 mRNA in a test sample, said kit comprising a nucleic acid hybridization assay probe that specifically hybridizes to DNA that is hypomethylated in cancer cells, said probe comprising SEQ ID NO:15 or a sequence having greater than 90% homolgy to SEQ ID NO:15 that encodes a complete human tsp50 protein.

17. A kit for identifying TSP50 mRNA comprising oligonucleotide primers that specifically amplify cDNA synthesized by reverse transcription of an mRNA from a test sample, said cDNA comprising SEQ ID NO:15 or a sequence having greater than 90% homology to SEQ ID NO:15 that encodes a complete human tsp50 protein.

18. The kit of claim 17 which comprises an oligonucleotide primer consisting of having SEQ ID NO:11 and an oligonucleotide primer consisting of SEQ ID NO:12.

* * * * *